(12) United States Patent
Nishiura et al.

(10) Patent No.: US 9,387,527 B2
(45) Date of Patent: Jul. 12, 2016

(54) METHOD AND APPARATUS FOR HOT-ROLLING METAL STRIP USING NEAR-INFRARED CAMERA

(75) Inventors: Nobuo Nishiura, Tokyo (JP); Takayuki Murata, Tokyo (JP); Koji Yanagino, Tokyo (JP); Kazuhiro Nitta, Tokyo (JP); Hiroshi Sawada, Tokyo (JP)

(73) Assignee: JFE Steel Corporation, Tokyo (JP)

( * ) Notice: Subject to any disclaimer, the term of this patent is extended or adjusted under 35 U.S.C. 154(b) by 884 days.

(21) Appl. No.: 12/528,520

(22) PCT Filed: Feb. 21, 2008

(86) PCT No.: PCT/JP2008/053457
§ 371 (c)(1),
(2), (4) Date: Aug. 25, 2009

(87) PCT Pub. No.: WO2008/105479
PCT Pub. Date: Sep. 4, 2008

(65) Prior Publication Data
US 2010/0095722 A1    Apr. 22, 2010

(30) Foreign Application Priority Data

| Feb. 28, 2007 | (JP) | 2007-050345 |
| Feb. 28, 2007 | (JP) | 2007-050346 |
| Feb. 28, 2007 | (JP) | 2007-050347 |
| Feb. 28, 2007 | (JP) | 2007-050348 |
| May 31, 2007 | (JP) | 2007-145399 |
| May 31, 2007 | (JP) | 2007-145493 |

(51) Int. Cl.
*B21B 1/26* (2006.01)
*B21B 37/74* (2006.01)
(Continued)

(52) U.S. Cl.
CPC . *B21B 1/26* (2013.01); *B21B 37/74* (2013.01); *B21B 38/006* (2013.01); *B21C 51/00* (2013.01);
(Continued)

(58) Field of Classification Search
CPC .... B21B 1/26; B21B 38/006; B21B 2261/20; B21B 37/74; B21B 45/004; G01N 3/18; G01N 2021/1731; G01K 1/026
USPC ............. 72/11.1, 11.3, 12.2, 11.7, 9.1, 37
See application file for complete search history.

(56) References Cited

U.S. PATENT DOCUMENTS 4,759,072 A    7/1988   Yamane et al.
5,687,595 A *  11/1997  Noe et al. ................. 72/8.3
(Continued)

FOREIGN PATENT DOCUMENTS

EP    0 153 565    9/1985
JP    05-30741     4/1993
(Continued)

OTHER PUBLICATIONS

English Translation of JP11156424A.*
English Translation of JP 11156424.*

*Primary Examiner* — Matthew G Katcoff
(74) *Attorney, Agent, or Firm* — RatnerPrestia

(57) ABSTRACT

A hot-rolling line, a method for photographing the entire width of a hot-rolled metal strip, a method for recording the photographic result of the entire width, a method for appropriately performing quality assurance, and a method for producing a hot-rolled metal strip using them, provide proper quality assurance for delivering a product to a customer. A hot-rolling line includes a near-infrared camera arranged to photograph an entire width of a hot-rolled metal strip on an entry side of a coiler of the hot-rolling line.

10 Claims, 14 Drawing Sheets

(51) Int. Cl.
  *G01K 1/02* (2006.01)
  *B21B 38/00* (2006.01)
  *B21C 51/00* (2006.01)
  *G01N 25/72* (2006.01)
  *B21B 45/00* (2006.01)
  *G01N 3/18* (2006.01)
  *G01N 21/89* (2006.01)
  *G01N 21/359* (2014.01)

(52) U.S. Cl.
  CPC ............... *G01K 1/026* (2013.01); *G01N 25/72* (2013.01); *B21B 38/00* (2013.01); *B21B 45/004* (2013.01); *B21B 2261/20* (2013.01); *G01N 3/18* (2013.01); *G01N 21/359* (2013.01); *G01N 2021/8918* (2013.01)

(56) References Cited

U.S. PATENT DOCUMENTS

| 6,286,349 B1* | 9/2001 | Muller et al. ................... 72/11.7 |
| 6,907,761 B2* | 6/2005 | Spence et al. ..................... 72/60 |
| 2006/0112753 A1* | 6/2006 | Friedman et al. ............... 72/426 |

FOREIGN PATENT DOCUMENTS

| JP | 6-007845 A | 1/1994 |
| JP | 11-156424 A | 6/1999 |
| JP | 2000-313920 A | 11/2000 |
| JP | 2001-321829 | 11/2001 |
| JP | 2003-311326 A | 11/2003 |
| JP | 2005-279665 A | 10/2005 |
| JP | 2005-288463 A | 10/2005 |

\* cited by examiner

FIG. 6

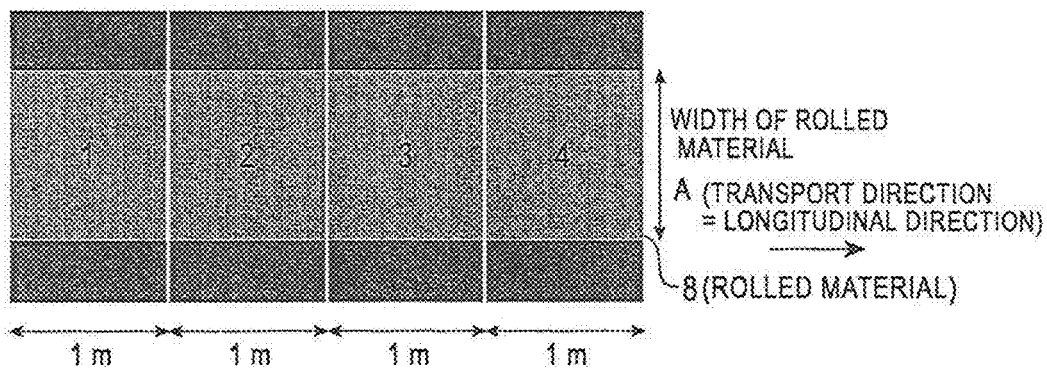

DETERMINATION IS MADE AT PITCH OF 1 m. BITS ARE ASSIGNED AS FOLLOWS: NG = 1; AND OK = 0. RESULTS OF QUALITY ASSESSMENT OF 4 m OF MATERIAL ARE EXPRESSED IN HEXADECIMAL NOTATION.

| REGION | | | | BINARY EXPRESSION | RESULT OF QUALITY ASSESSMENT (HEXADECIMAL EXPRESSION) |
|---|---|---|---|---|---|
| 1 | 2 | 3 | 4 | | |
| OK | OK | OK | OK | 0000 | 0 |
| OK | OK | OK | NG | 0001 | 1 |
| OK | OK | NG | OK | 0010 | 2 |
| OK | OK | NG | NG | 0011 | 3 |
| OK | NG | OK | OK | 0100 | 4 |
| OK | NG | OK | NG | 0101 | 5 |
| OK | NG | NG | OK | 0110 | 6 |
| OK | NG | NG | NG | 0111 | 7 |
| NG | OK | OK | OK | 1000 | 8 |
| NG | OK | OK | NG | 1001 | 9 |
| NG | OK | NG | OK | 1010 | A |
| NG | OK | NG | NG | 1011 | B |
| NG | NG | OK | OK | 1100 | C |
| NG | NG | OK | NG | 1101 | D |
| NG | NG | NG | OK | 1110 | E |
| NG | NG | NG | NG | 1111 | F |

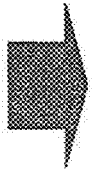

ONE DATA SET (1 TO F) FOR EVERY 4m IS TRANSMITTED TO BUSINESS COMPUTER OR THE LIKE.

(PRIOR ART)

FILM BOILING

NUCLEATE BOILING (PRIOR ART)

(PRIOR ART)

METHOD AND APPARATUS FOR HOT-ROLLING METAL STRIP USING NEAR-INFRARED CAMERA

RELATED APPLICATIONS

This is a §371 of International Application No. PCT/JP2008/053457, with an international filing date of Feb. 21, 2008 (WO 2008/105479 A1, published Sep. 4, 2008), which is based on Japanese Patent Application Nos. 2007-050345, 2007-050346, 2007-050347 and 2007-050348, all filed Feb. 28, 2007, and 2007-145399 and 2007-145493, both filed May 31, 2007.

TECHNICAL FIELD

This disclosure relates to a method and an apparatus for hot-rolling a metal strip while using a near-infrared camera and includes the following: installing a near-infrared camera capable of photographing the entire width of a metal strip in a metal strip hot-rolling line; photographing the entire width of a hot-rolled metal strip with the near-infrared camera before coiling the hot-rolled metal strip when a metal material is hot-rolled to form the hot-rolled metal strip (hereinafter, also referred to as a "rolled material"); recording the photographic result; determining the quality of the hot-rolled metal strip from the recorded result; and producing the hot-rolled metal strip using the result of the quality determination.

BACKGROUND

In general, a hot-rolling step includes the substeps of heating a slab-like metal material produced by continuous casting, ingot making, or blooming to several hundreds to a thousand and several hundreds of degrees centigrade in a furnace, lengthening the metal material with a roughing mill and a finishing mill to form a long, thin metal material, and coiling the resulting material.

FIG. 13 shows an example of a commonly used hot-rolling line 100. A metal material (hereinafter, referred to as a "material to be rolled") 8 having a thickness of 140 to 300 mm is heated to several hundreds to a thousand and several hundreds of degrees centigrade in a furnace 10 and is rolled with roughing mills 12 and a finishing mill 18, thereby forming a thin metal strip with a thickness of 0.8 to 25 mm.

In an exemplary structure shown in FIG. 13, two roughing mills 12 are arranged. Four roughing mills are commonly used. Furthermore, six roughing mills are used in some cases. The rolled material 8 is rolled with the roughing mills and then supplied to the finishing mill 18.

For example, the number of stands constituting the finishing mill 18 is seven in the exemplary structure shown in FIG. 13. In some cases, a finishing mill including six stands is used. The rolled material 8 having a temperature of several hundreds to a thousand and several hundreds of degrees centigrade is continuously rolled with the finishing mill 18 including the plural stands.

As shown in FIG. 13, a method in which a separate rolled material is rolled with the finishing mill 18 is referred to as batch rolling. In contrast, a method in which rolled materials are joined to each other and then rolled is referred to as endless rolling. It is more common to use the batch rolling.

The hot-rolling line 100 includes many (more than 100) table rolls (not shown) to transport the rolled material 8, except for the portions between the stands of the finishing mill 18.

Furthermore, the rolled material 8 has oxide layers (hereinafter, referred to as "scales") on front and back surfaces thereof when discharged from the furnace 10. The rolled material 8 that is in a high-temperature state is exposed to air, thereby forming new scales on the front and back surfaces. Thus, descaling devices 16 for removing the scales by blowing high-pressure water having a pressure of about 10 to 30 MPa on the front and back surfaces are arranged on the entry sides of the stands of the roughing mills 12, and the scales are removed.

Work rolls 19 are cooled by cooling water (not shown) because these come into contact with the high-temperature rolled material. Backup rolls 20 are also cooled by cooling water.

In FIG. 13, reference numeral 14 denotes a crop shear. This removes crops of leading and trailing ends of the rolled material 8 (distorted portions of the leading and trailing ends of the rolled material 8) by cutting before the finishing mill to form the rolled material having a substantially rectangular planar shape that can be smoothly fed to the finishing mill 18.

Reference numeral 50 denotes a controller. Reference numeral 70 denotes a process computer. Reference numeral 90 denotes a business computer.

Meanwhile, in recent years, metal strips rolled in the hot-rolling line 100 as shown in FIG. 13 have been required to have higher quality. A representative example is a metal strip. Recently, trends toward the reduction in the weight of automobiles have placed higher demand on high-tension steel and require higher quality.

In general, high-tensile steel is used to indicate a steel sheet having a tensile strength of 400 MPa or more. In recent years, high-tensile steel sheets have been required to have not only high tensile strength but also high processability such that they are not cracked when subjected to press forming or burring. Furthermore, any portion of a metal strip has been required to have uniformity in quality such as tensile strength and high processability.

To produce high-tensile steel sheets, the chemical composition of steel is adjusted. Even if any chemical composition is used, hot-rolling technology and production conditions are important for the production of a high-quality metal strip. In particular, important points are a temperature of the metal strip immediately before coiling with a coiler 24 subsequent to finish rolling, and uniformization of the temperature of the metal strip in the longitudinal and width directions.

In the exemplary hot-rolling line 100 shown in FIG. 13, a temperature of the rolled material 8 measured with a thermometer 25, arranged on the entry side of the coiler, immediately before coiling is the most important for quality assurance. It is important to control a run-out table 23 and cooling-related equipment 26 arranged there. Furthermore, a temperature of the rolled material 8 measured with a thermometer 21, arranged on the delivery side of a finishing mill, immediately after rolling is also important.

To equalize the temperature immediately before coiling to the extent possible, the temperature immediately before coiling the rolled material 8 needs to be measured across the entire width of the rolled material 8. To control the run-out table 23 and the cooling-related equipment 26, preferably, a temperature of the rolled material 8 immediately after finish rolling needs to be measured across the entire width of the rolled material 8.

Hitherto, infrared radiation thermometers are typically used for the thermometer 21 arranged on the delivery side of the finishing mill and the thermometer 25 arranged on the entry side of the coiler. These thermometers are fixedly arranged above the laterally central portion of the rolled material 8 and have a field of view of at most 20 to 50 mm.

That is, a temperature of only the laterally central portion of the rolled material 8 is measured as a representative over the entire length. A temperature distribution in the width direction is not measured.

Even if the result of the temperature measurement of only the laterally central portion of the rolled material 8 over the entire length meets quality assurance standards, there is no guarantee that a temperature of the rolled material 8 in the width direction meets the quality assurance standards.

In batch rolling, an uneven portion is within several tens of meters from the leading end of the rolled material 8 because the flatness control effect of the finishing mill 18 is not exerted yet. Furthermore, an uneven portion is within a hundred and several tens of meters, corresponding to the distance between the final stand of the finishing mill 18 and the coiler 24, from the leading or trailing end of the rolled material 8 because no tension is applied thereto. The portions have distorted wave shape. For example, as shown in FIG. 14, pools of cooling water are locally present in several places in a leading end region of the rolled material 8. In such a case, these places are locally cooled; hence, it is difficult to achieve a uniform temperature distribution in the width direction.

Meanwhile, with respect to a phenomenon occurring between a surface of steel and cooling water, a rolled steel material having a temperature of 550° C. or higher is in a state of film boiling in which the entire surface of the rolled material 8 is covered with a continuous film of steam as shown in FIG. 15. At less than about 550° C., the film of steam disappears, and then the state is transferred to a state of nucleate boiling in which cooling water is in direct contact with the rolled material 8 as shown in FIG. 15b. In the case where the temperature of the overall rolled material 8 is further reduced, the state is totally transferred to the state of nucleate boiling.

In a state in which film boiling and nucleate boiling coexist, heat transfer is promoted in a portion in the state of nucleate boiling compared with a portion in the state of film boiling. Thus, a temperature of the portion in the state of nucleate boiling is lower than that of another portion surrounding the portion, in some cases.

A target temperature of a high-tensile steel sheet immediately before coiling is often 550° C. or lower to ensure the quality. The temperature corresponds to a temperature range in which the transition from film boiling to nucleate boiling occurs. Thus, film boiling and nucleate boiling coexist in a portion and another portion surrounding the portion of the rolled material 8; hence, there are a portion where the cooling rate is high and a portion where the cooling rate is low.

In the portions where the water pools are present as described above; low-temperature parts (black spots) are locally present in the rolled material 8, thereby further increasing the difference in temperature of the rolled material 8 immediately before coiling between the portions where the water pools are present and portions where no water pool is present. This leads to unevenness in the quality of the rolled material 8 as a whole, so that the quality of localized portions may fall outside an allowable range.

Efforts have been made to measure a temperature distribution of the rolled material 8 in the width direction. In recent years, the measurement has been becoming increasingly important.

In the past, to measure the temperature distribution of the rolled material 8 in the width direction, a separate thermometer configured to scan the rolled material 8 in the width direction has been arranged in addition to a thermometer fixedly arranged at a position corresponding to the laterally central portion of the rolled material 8. The temperature measurement was performed in such a manner that the rolled material 8 was scanned in the width direction while being transported, i.e., diagonal loci were plotted on the rolled material 8. As shown in FIG. 16 which is a view of a hot-rolling line when viewed from above, thus, localized low-temperature black spots were not scanned or detected, in some cases.

Japanese Unexamined Patent Application Publication No. 2005-279665 describes that a temperature distribution of a steel strip in the width direction after controlled cooling is discretely measured over the entire length of the steel strip. As shown in FIGS. 17a and 17b, the timing of the occurrence of the temperature deviation of the steel strip in the width or longitudinal direction coincides with timing of the initiation or termination of the operation of cooling-related equipment, such as cooling banks, nozzles, and headers, in some cases. It is described that part of low-temperature region of the rolled material 8 in the entire length and width as indicated by a black frame shown in FIG. 17a is determined to be an abnormal portion and that the cooling device is also determined to be abnormal. In Japanese Unexamined Patent Application Publication No. 2005-279665, it is speculated from FIGS. 17a and 17b that the temperature of the rolled material 8 in the width direction is discretely measured at a pitch of 200 mm.

Japanese Unexamined Patent Application Publication No. 2003-311326 described that, in the case of a plate-rolling line, a temperature distribution of a steel sheet is measured with a near-infrared camera and a scan-type radiation thermometer arranged on the downstream side (delivery side) of a hot leveler. The aim is to minimize the deformation of steel sheet due to the release of residual stress by determining a residual stress distribution and adjusting conditions of heat treatment, which is a post-production step.

A near-infrared camera includes, for example, a two-dimensional matrix of square pixels. Temperature data measured with the pixels is subjected to linear interpolation to determine a pseudo-continuous temperature distribution of an object. Longitudinal and lateral dimensions of one pixel each are smaller than 200 mm, which is an example of the pitch used for the discrete temperature measurement described in Japanese Unexamined Patent Application Publication No. 2005-279665. Thus, it is possible to measure a temperature distribution in a more continuous manner.

In Japanese Unexamined Patent Application Publication No. 2003-311326, although it is unclear that which portion of a rolled material is subjected to temperature measurement and how large the portion is, it is clear that the temperature over the entire width is not measured. For example, mention is made of a steel sheet having a width of 3,000 mm. A near-infrared camera capable of measuring the entire width of the wide steel sheet having a width of as large as 3,000 mm was not developed at the time Japanese Unexamined Patent Application Publication No. 2003-311326 was filed, and the near-infrared camera is not yet developed.

Japanese Unexamined Patent Application Publication No. 2000-313920 describes that, in the case of a hot-rolling line for a metal strip, a temperature of a surface temperature of a steel sheet during transport is measured on an upstream side (entry side) of cooling-related equipment. The aim is to reduce temperature deviation and achieve uniform quality to the extent possible by performing cooling control with cooling water when the minimum surface temperature is equal to or lower than a predetermined value and when the deviation of the surface temperature is equal to or lower than a predetermined value, or by performing cooling control with a cooling gas when the deviation of the surface temperature exceeds the predetermined value.

Japanese Unexamined Patent Application Publication No. 2000-313920 does not describe a near-infrared camera serving as means for measuring the surface temperature of the steel sheet is. Furthermore, it is also unclear that which portion of a rolled material is subjected to temperature measurement and how large the portion is.

The technique disclosed in Japanese Unexamined Patent Application Publication No. 2005-279665 is based on the discrete temperature distribution measurement of a rolled material, the measurement being performed at a pitch of 200 mm. Like a traditional method in which a temperature of a rolled material is measured by scanning the rolled material in the width direction during transport, disadvantageously, a localized low-temperature portion, a black spot, is not detected, in some cases.

The technique disclosed in Japanese Unexamined Patent Application Publication No. 2003-311326 is targeted for a plate-rolling line. Furthermore, the entire width of a rolled material is not included in the measurement field of view. Thus, in the case where a localized low-temperature portion, a black spot, is present in a region out of the field of view, disadvantageously, the portion is not detected in the same way as above.

In the technique disclosed in Japanese Unexamined Patent Application Publication No. 2000-313920, from the viewpoint of the level of technology at the time the application was filed, there is a problem in which a shutter speed is not sufficiently fast. Furthermore, it is unlikely that the entire width of a rolled material is not included in the measurement field of view. Moreover, Japanese Unexamined Patent Application Publication No. 2000-313920 only describes the technique for controlling cooling with the cooling-related equipment by switching between water cooling and air cooling in a feedforward manner. A surface (two-dimensional) temperature distribution obtained as the result of the control is not measured. In addition, the measurement results are not recorded. Thus, disadvantageously, quality assurance for delivering a product to a customer cannot be provided.

It could therefore be helpful to provide a hot-rolling line, an electronic computer system configured to record a determination result of the quality of a hot-rolled metal strip, and an electronic computer system configured to control manufacture and quality histories and to control passing-step instructions, which provide proper quality assurance for delivering a product to a customer. In particular, these are characterized by assuredly detecting a localized low-temperature portion, a black spot.

SUMMARY

We thus provide:
1. A hot-rolling line includes a near-infrared camera arranged on an entry side of a coiler of the hot-rolling line, in which the near-infrared camera is capable of photographing an entire width of a hot-rolled metal strip.
2. The hot-rolling line described in item 1 further includes a near-infrared camera arranged on a delivery side of a finishing mill, in which the near-infrared camera is capable of photographing the entire width of the hot-rolled metal strip.
3. The hot-rolling line described in item 1 or 2 further includes a near-infrared camera arranged in the middle of a run-out table.
4. A method for photographing an entire width of a hot-rolled metal strip includes arranging a near-infrared camera at least one position selected from an entry side of a coiler of a hot-rolling line, a midway point of a run-out table, and a delivery side of a finishing mill, the near-infrared camera being capable of photographing the entire width of the hot-rolled metal strip, and taking a photograph.
5. The method for photographing the entire width of a hot-rolled metal strip described in item 4 further includes storing a luminance-temperature conversion curve showing a relationship between a luminance measured with the near-infrared camera and a temperature measured with a spot thermometer with respect to the same portion of the same heat source, i.e., a change in luminance as a temperature of the heat source is changed, before a temperature of a rolled material is measured by photographing the rolled material with the near-infrared camera arranged at least one position selected from the entry side of the coiler of the hot-rolling line, the midway point of the run-out table, and the delivery side of the finishing mill, the near-infrared camera being capable of photographing the entire width of the hot-rolled metal strip, and converting a luminance of an image of the rolled material photographed with the near-infrared camera arranged on the hot-rolling line into a temperature according to the luminance-temperature conversion curve.
6. The method for photographing the entire width of a hot-rolled metal strip described in item 4 further includes measuring a temperature of a rolled material by photographing the rolled material with the near-infrared camera arranged at least one position selected from the entry side of the coiler of the hot-rolling line, the midway point of the run-out table, and the delivery side of the finishing mill, the near-infrared camera being capable of photographing the entire width of the hot-rolled metal strip, measuring a temperature of a portion of the rolled material with a spot thermometer arranged at the position where the near-infrared camera is arranged, the portion being in the field of view of the near-infrared camera, calibrating the near-infrared camera in such a manner that the temperature of the portion of the rolled material measured with the near-infrared camera coincides with the temperature of the same portion measured with the spot thermometer, and photographing the rolled material.
7. The method for photographing the entire width of a hot-rolled metal strip described in item 4 further includes adjusting a shutter speed in response to a temperature of the hot-rolled metal strip when the entire width of the hot-rolled metal strip is photographed with the near-infrared camera arranged on the entry side of the coiler of the hot-rolling line.
8. The method for photographing the entire width of a hot-rolled metal strip described in item 4 further includes slowing down the shutter speed in such a manner that a sufficient resolution of the temperature measured by photographing the entire width of the hot-rolled metal strip with the near-infrared camera is achieved.
9. The method for photographing the entire width of a hot-rolled metal strip described in any one of items 4 to 8 further includes photographing an entire length of the hot-rolled metal strip.
10. A method for recording the photographic result of an entire width of a hot-rolled metal strip includes recording a photographic result obtained by the method described in any one of items 4 to 9.

11. A method for determining the quality of a hot-rolled metal strip includes determining the quality of a hot-rolled metal strip by a photographic result of an entire width or an entire length of the hot-rolled metal strip with a near-infrared camera arranged on an entry side of a coiler of a hot-rolling line.

12. The method for determining the quality of a hot-rolled metal strip described in item 11 further includes recording a determination result of the quality of the hot-rolled metal strip, the quality being determined by the photographic result of the entire width or the entire length of the hot-rolled metal strip with a near-infrared camera arranged on the entry side of the coiler of the hot-rolling line.

13. A method for producing a hot-rolled metal strip by employing the method described in item 11 or 12.

14. An electronic computer system configured to record a determination result of the quality of a hot-rolled metal strip includes a near-infrared camera capable of photographing an entire width of a hot-rolled metal strip in a hot-rolling line.

15. An electronic computer system configured to control manufacture and quality histories and to control passing-step instructions of a hot-rolled metal strip on the basis of a determination result of the quality of the hot-rolled metal strip includes a near-infrared camera capable of photographing an entire width of the hot-rolled metal strip in a hot-rolling line.

16. The electronic computer system configured to record the determination result of the quality of a hot-rolled metal strip described in item 14, in which the near-infrared camera photographs the entire length of the hot-rolled metal strip.

17. The electronic computer system configured to control manufacture and quality histories and to control passing-step instructions of a hot-rolled metal strip described in item 15, in which the near-infrared camera photographs an entire length of the hot-rolled metal strip.

18. A method for cutting out a defective quality portion of a hot-rolled metal strip in a downstream step using the system described in any one of items 14 to 17.

Accordingly, there are provided a hot-rolling line, a method for photographing the entire width of a hot-rolled metal strip, a method for recording the photographic result of the entire width, a method for appropriately performing quality assurance, and a method for producing a hot-rolled metal strip using them, which provide proper quality assurance for delivering a product to a customer. Furthermore, we provide an electronic computer system configured to record a determination result of the quality of a hot-rolled metal strip and an electronic computer system configured to control manufacture and quality histories and to control passing-step instructions.

BRIEF DESCRIPTION OF DRAWINGS

FIG. 6 shows the illustration of one of our structures.

Figure 1:
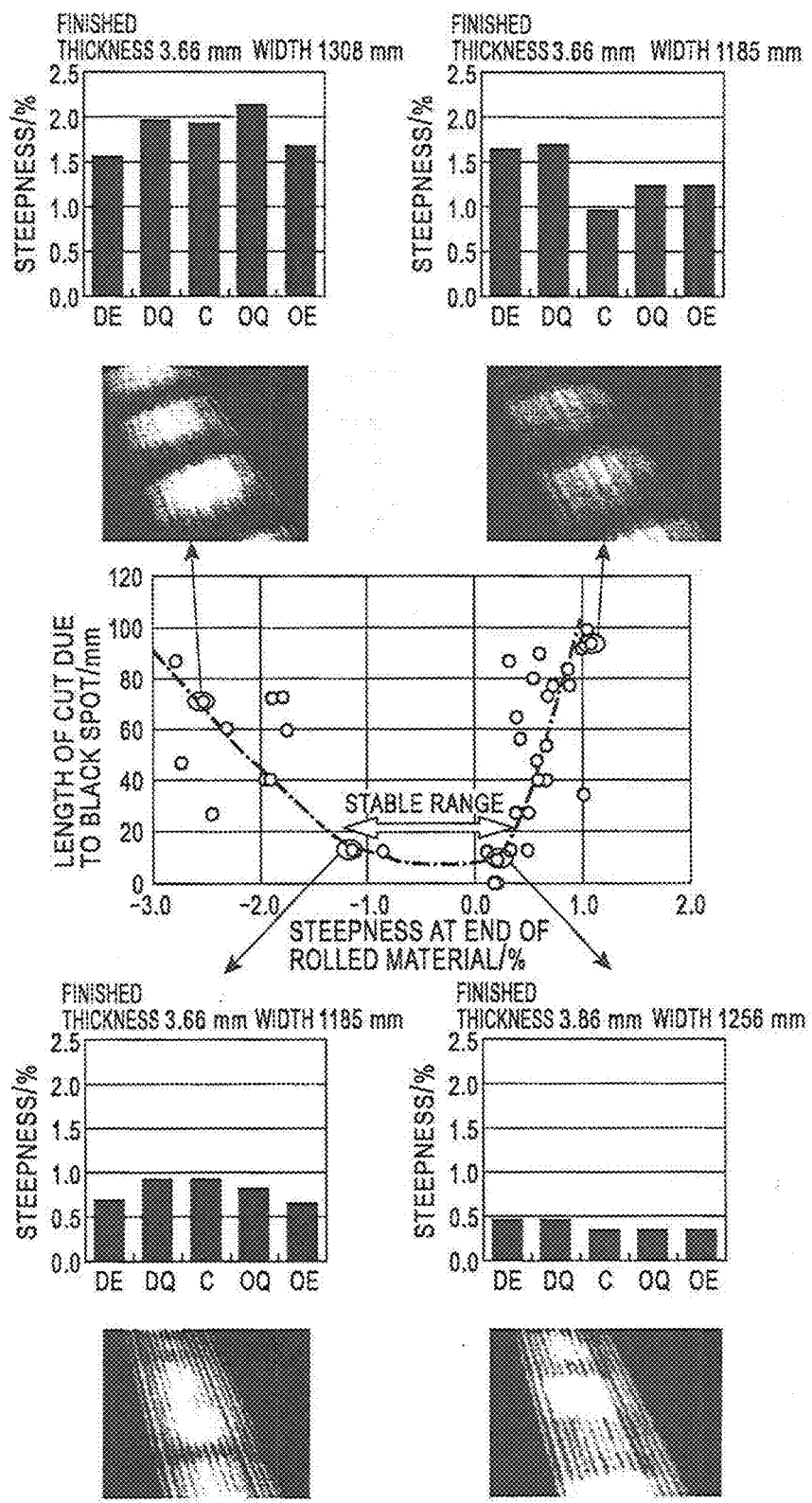
FIG. 1 shows the relationship between poor flatness (steepness) of an end, e.g., edge waves and center buckles, and cut-out length.

Reference numerals in the drawings are defined as follows:
5 shear
6 welder
8 rolled material
10 furnace
12 roughing mill
135 edger roll
14 crop shear
15 thermometer arranged on entry side of finishing mill
18 finishing mill
19 work roll
20 backup roll
21 thermometer arranged on delivery side of finishing mill
21A near-infrared camera
22 thickness gauge on delivery side of finishing mill
23 run-out table
24 coiler
25 thermometer arranged on entry side of coiler
25A near-infrared camera
251 dedicated personal computer
252 private LAN
253 personal computer in office
26 cooling-related equipment
27 thermometer located at intermediate point
27A near-infrared camera
30 in-line skin pass
50 controller
70 process computer
90 business computer
100 hot-rolling line
200 pickling line
900 electronic computer system
901 electronic computer system
A transport direction

DETAILED DESCRIPTION

A portion with a black spot needs to be cut out because of its poor mechanical properties, such as elongation stretch and frangibility, of a metal strip serving as a product. Only a metal strip including a portion with a negligible black spot should be delivered to a customer.

To prevent the misdelivery of a rolled material having a black-spot portion to a customer and give quality assurance, it is necessary to perform quality determination in which the portion of the rolled material with the black spot is accurately distinguished as a localized portion having a low temperature.

Figure 9A:
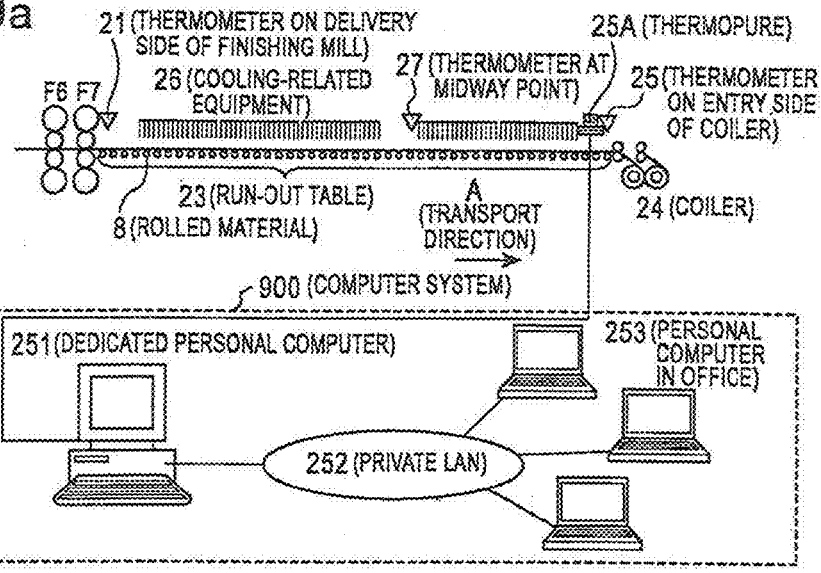
FIGS. 9a, 9b, 9c, and 9d each show illustrations of our structures.

To that end, as shown in FIG. 9a, a near-infrared camera capable of photographing the entire width of a rolled material 8 is preferably arranged on the entry side of a coiler. Alternatively, the near-infrared camera may be arranged at an intermediate position of a run-out table or on the delivery side of a finishing mill. Furthermore, as shown in each of FIGS. 9b, 9c, and 9d, near-infrared cameras may be arranged at a plurality of positions among them.

The near-infrared camera arranged on the entry side of the coiler is preferably arranged at a position (entry side) located within 30 m from the center of a mandrel (not shown) of a coiler 24, which is located in the upstream direction of the transport of the rolled material 8, in the upstream direction of the transport of the rolled material 8.

In the case of arranging the near-infrared camera on the delivery side of the finishing mill, the near-infrared camera is preferably arranged at a position (delivery side) located within 30 m from the center of a work roll of the final stand of a finishing mill 18 in the transport direction of the rolled material 8.

In the case of arranging the near-infrared camera at the intermediate position of the run-out table, the near-infrared camera is preferably arranged therebetween.

FIG. 1 shows the relationship between poor flatness (steepness) in a leading end region, e.g., a) edge waves and b) center buckles, and cut-out length.

As is apparent from FIG. 1, in the case where portions having black spots of the rolled material 8 extend in the longitudinal direction due to poor flatness (steepness) in the leading end region, e.g., a) edge waves and b) center buckles, it is necessary to increase the cut-out length when the entire length of each of the portions having the significant black spots is cut out in a downstream step such as pickling.

With respect to the longitudinal direction of the rolled material 8, it is thus preferable to photograph a region including an uneven portion which is located within several tens of meters from the leading end of the rolled material 8 and on which the flatness control effect of the finishing mill 18 is not exerted yet or including an uneven portion which is located within a hundred and several tens of meters, corresponding to the distance between the final stand of the finishing mill 18 and the coiler 24, from the leading or trailing end of the rolled material 8 and to which no tension is applied.

Of course, it is also preferable to photograph the entire length of the rolled material 8.

Images shown in FIG. 1 are taken as follows: a near-infrared camera is temporarily arranged at a position located one meter from a thermometer 25 on a hot-rolling line 100 in the upstream direction so as to face toward the finishing mill 18, the thermometer 25 being provided on an entry side of the coiler, and then the images are taken. A target tensile strength, which is a typical mechanical property, is 590 MPa. A target coiling temperature is 470° C. at the position of the thermometer 25. In the figure, D represents a drive side, O represents an operator side (opposite the drive side), C represents a central portion, Q represents a quarter portion, and E represents an edge. Values of steepness are measured at a position located 53 m from the leading end of the rolled material 8 in the longitudinal direction.

In the leading end region and a trailing end region (with a length corresponding to the distance between the final stand F7 of the finishing mill 18 and the coiler 24) of the rolled material 8 where sometimes have poor flatness, continuous images are preferably captured at least over the entire length thereof in the longitudinal direction.

Of course, it is also preferable to capture continuous images of the entire length of the rolled material 8 to the extent possible.

Figure 2:
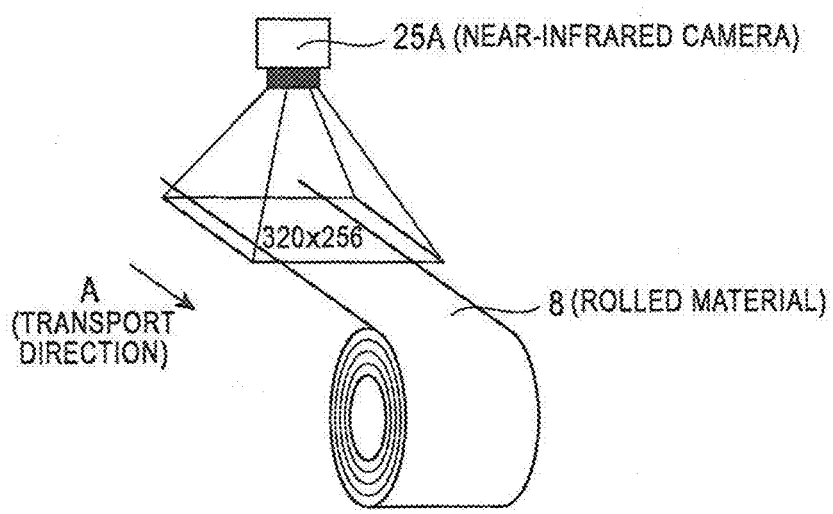
FIG. 2 shows an example of the arrangement of a near-infrared camera.

In the near-infrared camera used herein, a single pixel is 30 μm long by 30 μm wide. The near-infrared camera has a 320 by 256 matrix of pixels. As an example of arrangement shown in FIG. 2, in the case where the rolled material 8 is photographed from directly above, in terms of not the near-infrared camera but the target rolled material 8, a region having a size of 10 mm×10 mm per pixel, in other words, a region having a length of 3,200 mm (in the longitudinal direction) and a width of 2,560 mm (in the width direction) in total can be captured in the field of view at a time.

Each of the dimensions of the target rolled material 8 per pixel is preferably 10 mm or less. The reason for this is that at a dimension exceeding this value, a captured image is jagged, so that it is difficult to recognize the outer edge and the planar shape of a black spot.

The lower limit of each dimension need not be specified. A lower limit of each dimension of 10 mm or more will suffice.

Hitherto, the maximum width of rolled materials commonly manufactured is 2,300 mm. The field of view of the near-infrared camera can include entire widths of all types of rolled material 8.

Figure 3A:
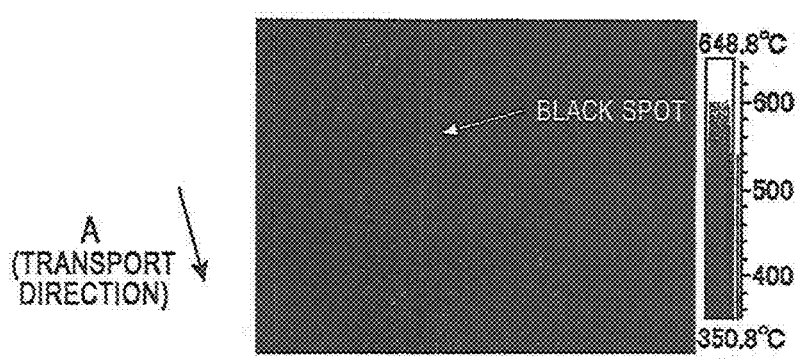
FIG. 3a shows a normal image captured with a near-infrared camera.

FIG. 3a, which is an image captured by the temporarily arranged near-infrared camera, shows the case where an image can be properly captured. The transport speed of the rolled material 8 is in the range of 120 mpm to 1,200 mpm in the exemplary hot-rolling line 100. The field of view of the near-infrared camera is 3,200 mm in length (longitudinal direction). For example, if the transport speed of the rolled material 8 is 1,200 mpm, it takes 0.16 sec to transport it for 3,200 mm. Thus, images are taken once every 0.16 sec. Shooting is started before the leading end of the rolled material 8 enters the field of view, and completed after the entire length of the rolled material 8 is transported and then the trailing end exits from the field of view. In the case where the transport speed is lower, a shooting interval may be increased so as to be inversely proportional to the transport speed.

Figure 3B:
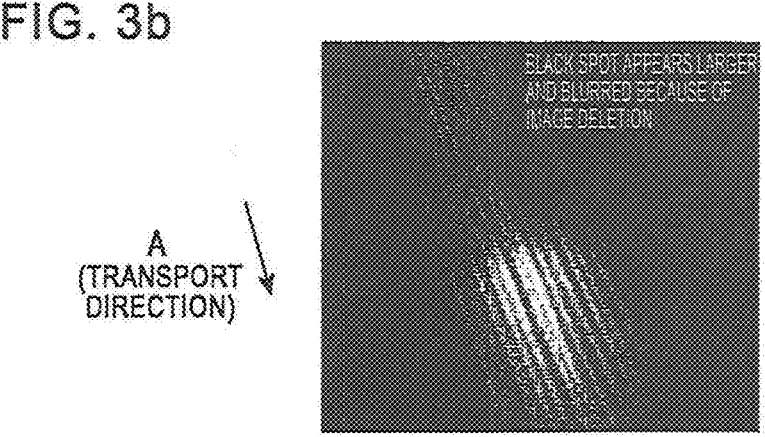
FIG. 3b shows a blurred image captured with the near-infrared camera.

In the case of using a near-infrared camera in which a shutter speed in one shooting is on the order of milliseconds, which is not sufficiently high, when the transport speed of the rolled material 8 is high, a black spot may appear larger and blurred because of image deletion, as shown in FIG. 3b.

In this example, a near-infrared camera that meets the specifications shown in Table 1 is used. Use of a high-shutter-speed near-infrared camera with a fastest shutter speed of 10 μsec (one hundred-thousandth of a second) enables us to take pictures that are not blurred even if the transport speed of the rolled material 8.

TABLE 1

| Item | Specification |
| --- | --- |
| Element | InGaAs |
| Measurement wavelength | 0.9 to 1.7 μm |

TABLE 1-continued

| Item | Specification |
| --- | --- |
| Number of pixel | 320 × 256 |
| Lens | Focal length: 8 mm, angle of view: 60° |
| Height from pass line | 2.8 mm |
| Resolution | 10 mm/pixel |
| Measurable temperature range | 300° C. to 750° C. |
| Shutter speed | 10 μsec to 50 μsec |

Figure 4A:
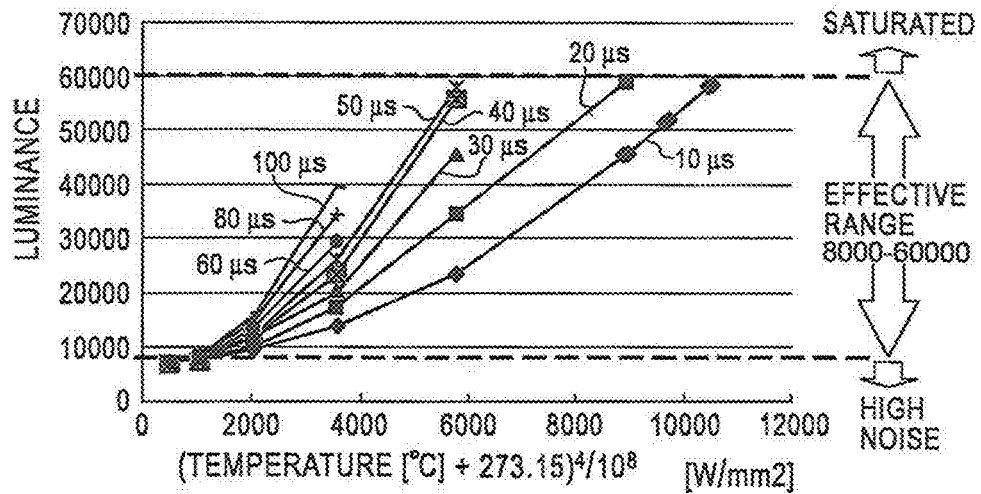
FIG. 4a shows the relationship between the temperature and the luminance when the shutter speed of a near-infrared camera is changed.

FIG. 4a shows the relationship between the temperature and the luminance when the shutter speed of the near-infrared camera is changed. The horizontal axis represents radiant heat energy (W/mm$^2$) into which the temperature of the rolled material 8 is converted. The vertical axis represents the luminance ([−]).

With respect to the near-infrared camera used, in a region with a luminance of less than 8,000 ([−]), it is difficult to obtain clear images because of a significant influence of noise. The lower limit of the luminance is thus set to 8,000 ([−]).

Furthermore, according to the specifications of the near-infrared camera, the luminance is measured using a 16-bit signal, so that a region with a luminance exceeding a maximum luminance of $2^{16}$=65,536 ([−]) cannot be measured because of saturation. To provide an adequate margin of safety, the upper limit is thus set to 60,000 ([−]).

A measurable range is located between the upper limit and the lower limit described above. A temperature range corresponding to the range is defined as a measurable temperature range. The relationship will be clearly described below.

Figure 4B:
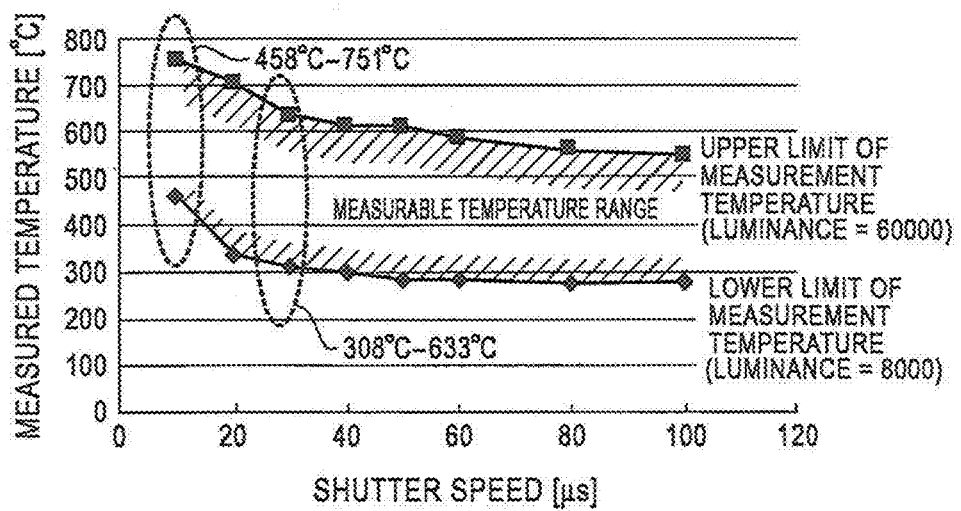
FIG. 4b shows the relationship between the shutter speed and the measurable temperature range.

FIG. 4b shows the relationship between the shutter speed and the measurable temperature range. The results demonstrate the following: In the case of using a faster shutter speed, at a shutter speed of less than about 40 μsec, a temperature of the rolled material 8 having a temperature of less than 300° C. cannot be measured. A still faster shutter speed causes an increase in the lower limit of the measurable temperature range.

In the case where the rolled material 8 is high-tensile steel, although a target temperature immediately before coiling varies depending on the type of steel, the temperature of the rolled material 8 after cooling with cooling-related equipment 26 reaches 300° C. at a minimum, in some cases.

To enable a minimum temperature of 300° C. to be measured regardless of the type of the rolled material 8, the shutter speed needs to be set to 40 μsec or more. The shutter speed is preferably adjusted in response to the temperature of the rolled material 8.

That is, for example, in the case where a target temperature of the rolled material 8 immediately before coiling is a measurable low temperature close to 300° C., the shutter speed of the near-infrared camera is preferably set to, for example, 40 μsec or more (in the near-infrared camera, the slowest shutter speed is 50 μsec according to the specifications shown in Table 1) to the extent that an image is not blurred. In the case where a target temperature of the rolled material 8 immediately before coiling is a high temperature, e.g., 450° C. to 750° C., the shutter speed of the near-infrared camera is preferably set to, for example, less than 40 μsec (in the near-infrared camera, the fastest shutter speed is 10 μsec according to the specifications shown in Table 1). It is preferred to ensure the measurable temperature range.

Needless to say, the radiant energy is reduced as the temperature of the rolled material 8 approaches the lower limit of the measurable range. Thus, the shutter speed is preferably slowed down so as to ensure the measurable temperature range. In the case where the temperature of the rolled material 8 approaches the upper limit of the measurable temperature range, a faster shutter speed is preferably used to the extent possible, so that the state of the rolled material transported at high speed can be photographed instantaneously, thus preventing the blurring of an image.

The shutter speed of the near-infrared camera is preferably determined in advance in response to a target temperature immediately before coiling, the target temperature being determined by the type of the rolled material 8. Alternatively, the shutter speed is preferably adjusted in response to an actual temperature of the leading end of the rolled material 8 measured with a thermometer 21 arranged on the entry side of the finishing mill.

Near-infrared cameras can measure not temperature but luminance. Some near-infrared cameras include logic to convert luminance into temperature in some way, the logic being incorporated by manufacturers. In this case, the converted temperature sometimes has a maximum error of about 20° C.

To overcome this problem, the relationship between a luminance measured with the near-infrared camera and a temperature measured with a spot thermometer in the off-line with respect to the same portion of the same heat source is determined as a luminance-temperature conversion curve in advance. This is stored in a controller 50, a process computer 70, or the like. A luminance obtained by photographing a rolled material with the near-infrared camera arranged on the hot-rolling line is converted into a temperature according to the luminance-temperature conversion curve.

Figure 3C:
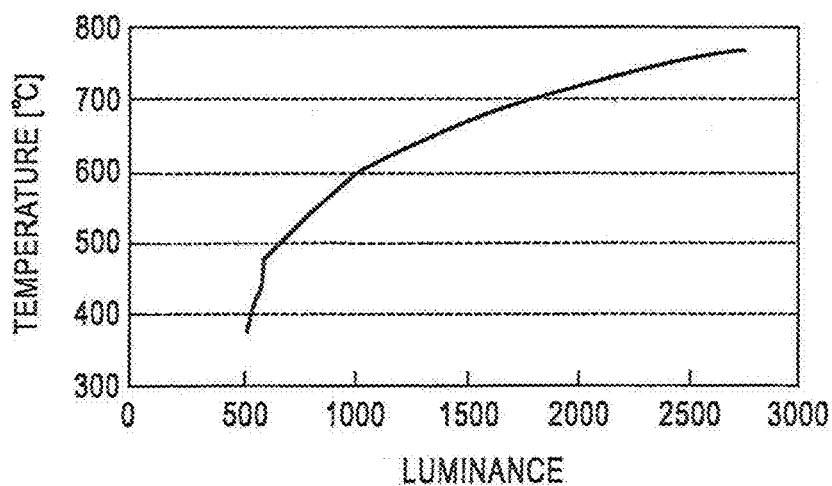
FIG. 3c shows a luminance-temperature conversion curve.

FIG. 3c shows the results. A scale indicated on the right side of FIG. 3a shows the relationship between tints of color and temperature. Alternatively, there is a method including measuring a temperature of the same portion of a rolled material with the near-infrared camera and the spot thermometer, calibrating the near-infrared camera in such a manner that the temperature of the portion of the rolled material measured with the near-infrared camera coincides with the temperature of the same portion measured with the spot thermometer, and photographing the rolled material. This method can also be referred to as on-line calibration.

Figure 9B:
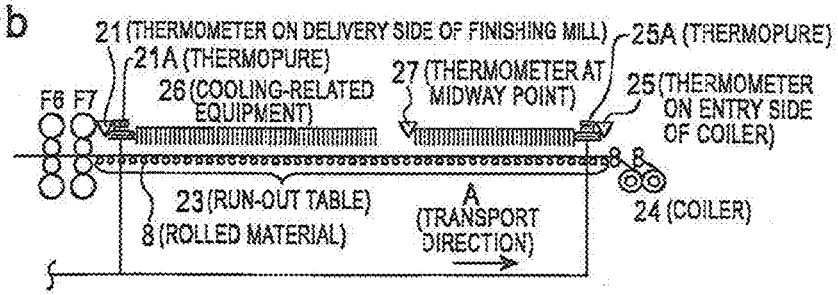
Figure 9C:
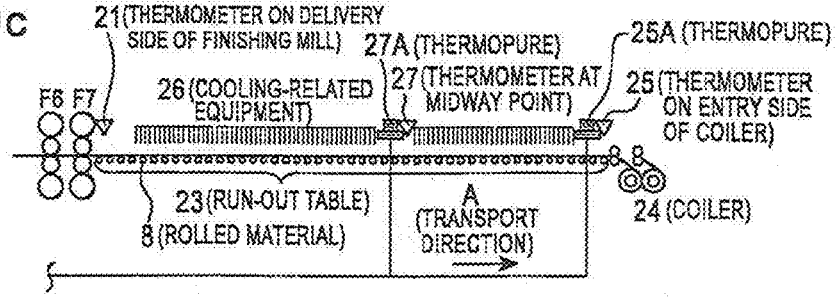
Figure 9D:
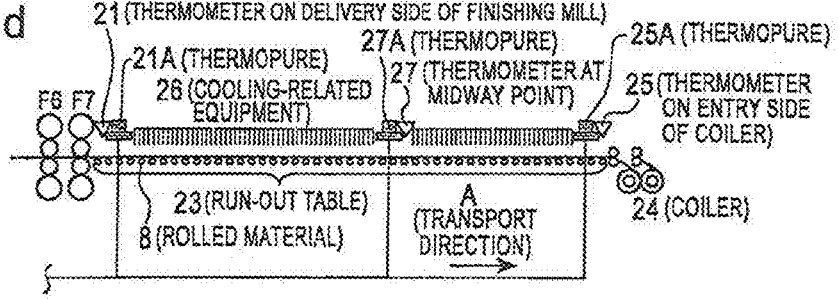

FIG. 9a shows an exemplary arrangement in which a near-infrared camera 25A is located adjacent to the thermometer 25 arranged on the entry side of a coiler. The orientation of the thermometer 25, which is a spot thermometer, arranged on the entry side of the coiler is adjusted so as to measure a temperature of a portion of the rolled material located in the field of view of the near-infrared camera. FIG. 9b shows an exemplary arrangement in which a near-infrared camera 21A and the near-infrared camera 25A are located adjacent to the thermometer 21 arranged on the delivery side of a finishing mill and the thermometer 25 arranged on the entry side of the coiler, respectively. FIG. 9c shows an exemplary arrangement in which a near-infrared camera 27A and the near-infrared camera 25A are located adjacent to a thermometer 27 located at an intermediate point and the thermometer 25 arranged on the entry side of the coiler, respectively. FIG. 9d shows an exemplary arrangement in which the near-infrared cameras 21A, 27A, and 25A are located adjacent to the thermometer 21 arranged on the delivery side of the finishing mill, the thermometer 27 located at the intermediate point, and the thermometer 25 arranged on the entry side of the coiler, respectively. The orientations of the thermometer 21 arranged on the delivery side of the finishing mill and the thermometer 27 located at the intermediate point, which are spot thermometers, are adjusted in the same way as above.

In the case where the field of view of the spot thermometer is larger than the size of a pixel of the near-infrared camera and where plural pixels of the near-infrared camera are included in the field of view of the spot thermometer, preferably, a luminance-temperature conversion curve is determined or the near-infrared camera is calibrated in such a manner that a representative pixel is selected and then a temperature measured with the spot thermometer coincides with a temperature measured at the pixel. Alternatively, another method may be employed in which a mean value coincides.

How quality is determined on the basis of a planar (two-dimensional) temperature distribution of the rolled material 8 measured with the near-infrared camera will now be described by taking the case of a temperature distribution obtained by photographing the entire width and length of the rolled material 8 as an example.

Figure 5:
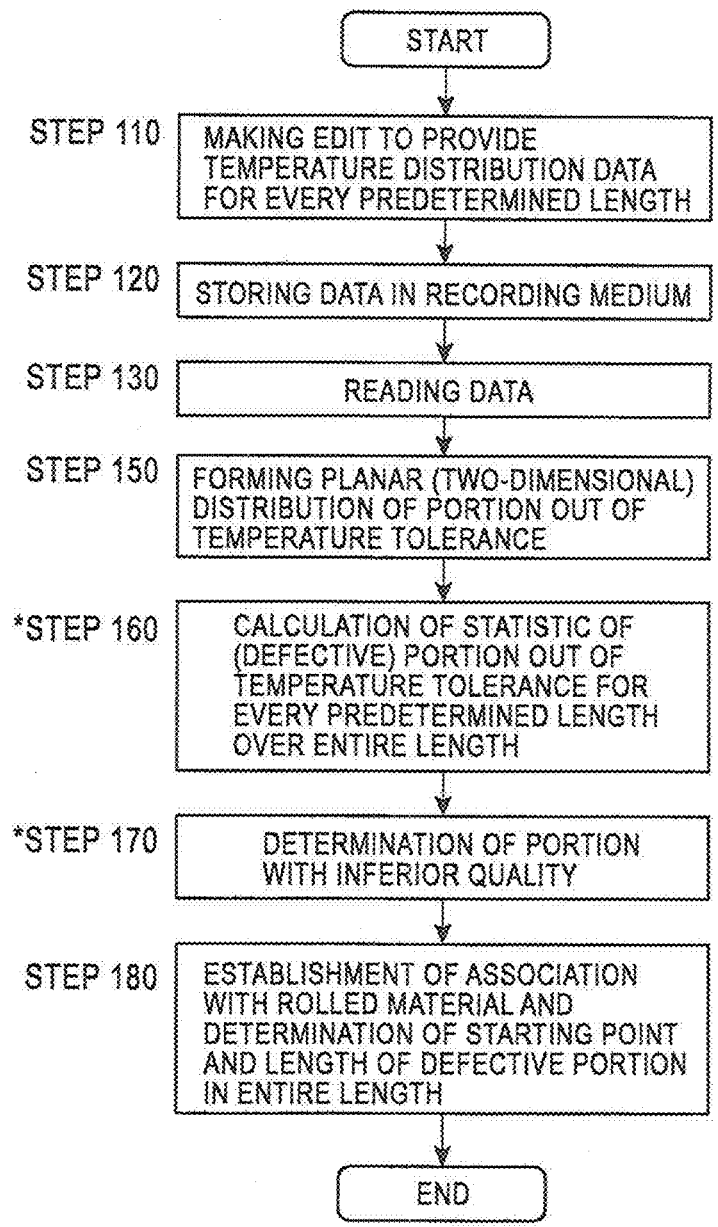
FIG. 5 shows the illustration of one of our structures.

The entire sequence will be described with reference to steps shown in FIG. 5.

As described above, in the case where the transport speed of the rolled material 8 is 1,200 mpm, shooting is performed for every 0.16 sec, so that the temperature distribution data of the entire width and length is measured for every 3,200 mm in the transport direction, i.e., in the longitudinal direction of the rolled material 8.

The shooting of the rolled material 8 is completed, i.e., the shooting is performed up to the trailing end of the rolled material 8. To facilitate post-processing, the temperature distribution data of the entire width and length of the rolled material 8 is temporarily stored in a recording medium such as memory of a computer such as a personal computer. The data is edited to provide temperature distribution data for every predetermined length, e.g., 4 m (4,000 mm), in the longitudinal direction of the rolled material 8 (step 110).

The data is stored in a recording medium such as a hard disk drive of the computer such as a personal computer (step 120).

The data is read and temporarily stored in the recording medium such as memory of the computer such as a personal computer (step 130).

Whether each of the pixels in one unit or in one image is within a temperature tolerance is determined. A pixel showing a temperature exceeding the upper limit of the temperature tolerance (upper temperature threshold), a pixel showing a temperature less than the lower limit of the temperature tolerance (lower temperature threshold), and the planar (two-dimensional) coordinates (representative values or length-breadth ranges) of these pixels are temporarily stored to form a planar (two-dimensional) distribution of portions out of the temperature tolerance (step 150).

Various statistics of defective-quality portions of the rolled material 8 out of the temperature tolerance are calculated over the entire length for every predetermined length, i.e., for every unit described above (step 160).

The determination of the defective-quality portions of the rolled material 8 out of the temperature tolerance is performed, for example, for every 1 m on the basis of the various statistics. Furthermore, for example, the determination results of the quality are expressed in hexadecimal notation as shown in FIG. 6 to form information bits over the entire length (step 170).

Finally, the starting point and the length of each of the defective-quality portions of the rolled material 8 out of the temperature tolerance from the leading end of the rolled material 8 are determined. The data sets are associated with the rolled material 8 and stored in a recording medium such as a hard disk drive of the computer such as a personal computer (step 180).

Calculation processes of the statistics in (step 160) are described below.

For example, the statistics calculated are as follows.

(1) Ratio of Out-of-Tolerance Area

Figure 7A:
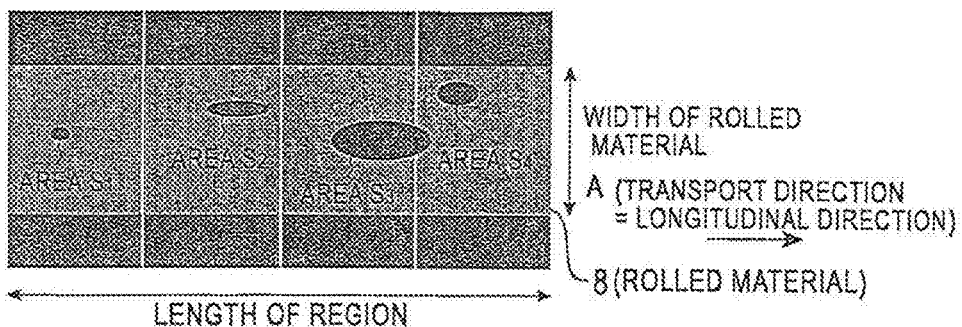
FIGS. 7a, 7b, 7c, and 7d show defective quality portions of a rolled material 8 outside a temperature tolerance when the rolled material 8 is viewed from the above.

The ratio of areas of the defective-quality portions of the rolled material 8 out of the temperature tolerance to the area of the rolled material 8 when viewed from above is defined as the ratio (%) of the out-of-tolerance area, as shown in FIG. 7*a*.

A calculation formula is as follow:

Ratio of out-of-tolerance area=Σareas $S_i$ of out-of-tolerance portions/(length of region×width of rolled material)×100(%)   (1).

(2) Ratio of Out-of-Tolerance Length

Figure 7B:
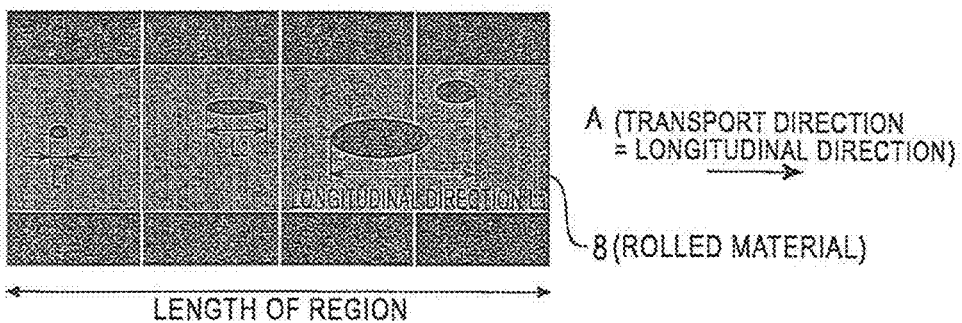

The ratio of the length of the defective-quality portions of the rolled material 8 out of the temperature tolerance in the longitudinal direction to the length of the rolled material 8 when viewed from above is defined as the ratio of the out-of-tolerance length (%), as shown in FIG. 7*b*. With respect to portions that overlap each other in the longitudinal direction, the overlapping part is not counted twice. The overlapping portions are regarded as a single portion. Then the length thereof is determined, and calculation is performed ($L_3$ in FIG. 7*b*).

A calculation formula is as follow:

Ratio of out-of-tolerance length=Σout-of-tolerance lengths $L_i$/length of region   (2).

(3) Out-of-Tolerance Mean Number

Figure 7C:
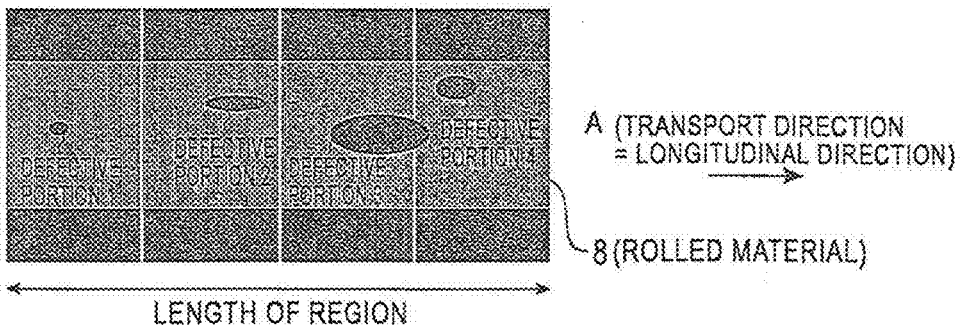

The number of the defective-quality portions of the rolled material 8 per number of images N (in this example, N=4) is defined as an out-of-tolerance mean number, as shown in FIG. 7*c*.

A calculation formula is as follow:

Out-of-tolerance mean number=number of out-of-tolerance portions/number of images $N$ (number/fixed pitch of 4 m)   (3).

(4) Mean Area of Out-of-Tolerance Portion/Portion

Figure 7D:
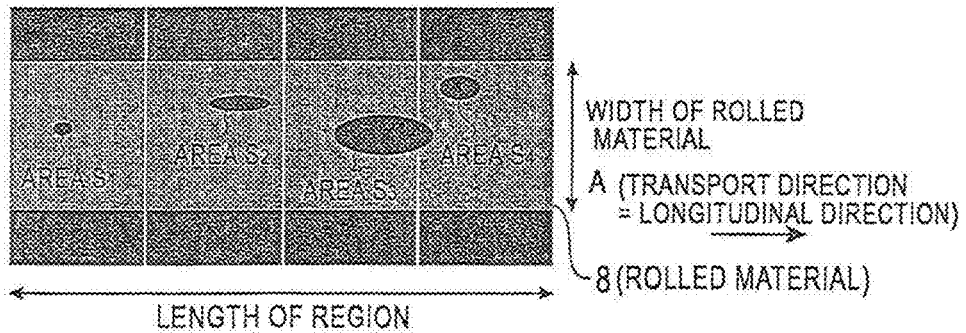

The quotient when the total area of the defective-quality portions of the rolled material 8 out of the temperature tolerance is divided by the number of the defective-quality portions is defined as the mean area of the out-of-tolerance portion/portion, as shown in FIG. 7*d*.

A calculation formula is as follow:

Mean area of out-of-tolerance portion/portion=area of out-of-tolerance portions $S_i$/number of out-of-tolerance portions   (4).

Meanwhile, processes for determining the defective-quality portions and their length in (step 170) are described below. In this example, (1) to (3) are performed for every fixed length, i.e., at a pitch of 4 m, of the rolled material. In particular, (4) and (5) need to be performed in detail and thus are performed for every 1 m of the rolled material.

(1) Determination Based on Ratio of Out-of-Tolerance Area

In the case where the result of the calculation using formula (1) described above (in this example, the length of the region=4 m) is a threshold $S_{NG1}$ or more, the quality of the unit (4 m) of the rolled material is determined to be failure (NG).

(2) Determination Based on Ratio of Out-of-Tolerance Length

In the case where the result of the calculation using formula (2) described above (in this example, the length of the region=4 m) is a threshold $L_{NG}$ or more, the quality of the unit (4 m) of the rolled material is determined to be failure (NG).

(3) Determination Based on Out-of-Tolerance Mean Number

In the case where the result of the calculation using formula (3) described above (in this example, the number of images N=4) is a threshold $N_{NG}$ or more, the quality of the unit (4 m) of the rolled material is determined to be failure (NG).

(4) Determination Based on Mean Area of Out-of-Tolerance Portion/Portion

Figure 8A:
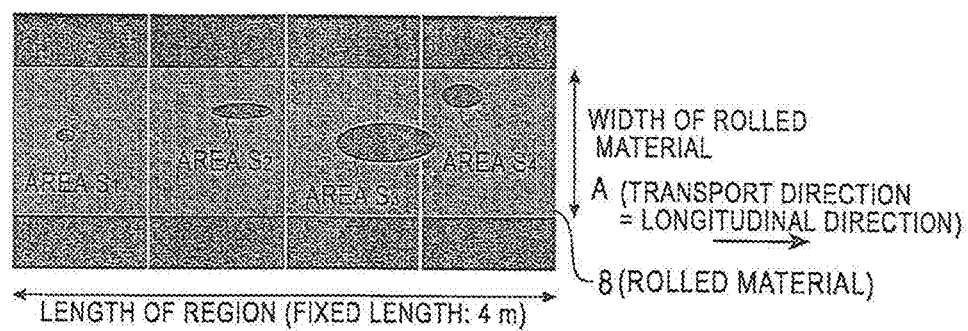
FIGS. 8a and 8b show defective quality portions of the rolled material 8 outside a temperature tolerance when the rolled material 8 is viewed from the above.

In the case where any of the areas $S_i$ of the out-of-tolerance portions is a threshold $S_{NG2}$ or more, the quality is determined to be failure (NG) for every 1 m of the rolled material, as shown in FIG. 8a. (Note that this is different from formula (4) described above. This is not so hard because an item used in the course of the calculation using formula (4) described above is used for the determination).

Figure 8B:
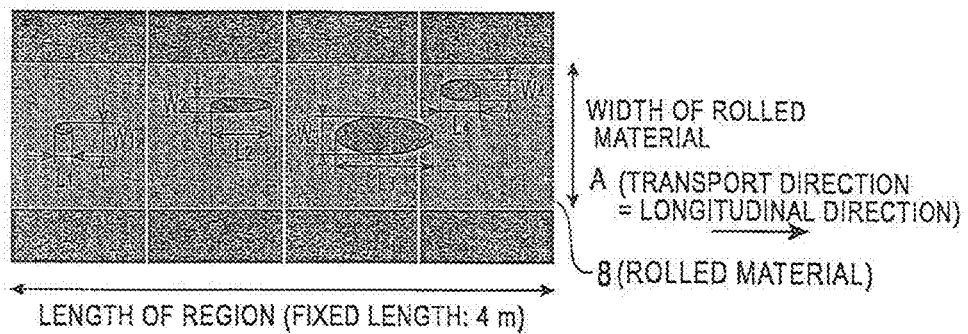

(5) Determination Based on Dimensions of Single Out-of-Tolerance Portion in Longitudinal and Width Directions In the case where any of out-of-tolerance portions having a longitudinal dimension of a threshold $L_{NG}$ or more is present or where any of out-of-tolerance portions having a width dimension of a threshold $W_{NG}$ or more is present, the quality is determined to be failure (NG) for every 1 m of the rolled material, as shown in FIG. 8b.

In the example described above, the upper temperature threshold, the lower temperature threshold, the threshold $S_{NG1}$ of the rate of the areas of the out-of-tolerance portions, the threshold $L_{NG}$ of the longitudinal dimension of the out-of-tolerance portions, the threshold $W_{NG}$ of the width dimension of the out-of-tolerance portions, the threshold $N_{NG}$ of the number of the out-of-tolerance portions, the threshold $S_{NG2}$ of the area per out-of-tolerance portion, and the like may be stored in, for example, the process computer 70 for each type and dimension of the rolled material 8 and may be transmitted to a business computer 90 or a personal computer, as needed. Alternatively, these thresholds may also be transmitted to a near-infrared camera via the controller 50, as needed.

Meanwhile, in the case of batch rolling, as described above, the uneven portion is located within several tens of meters to a hundred and several tens of meters from the leading end or the trailing end of the rolled material 8. Thus, the following method may be employed. In the uneven portion, a tens-of-meter part is always out of tolerance and is thus cut out in the downstream process. The cut-out part is not subjected to quality determination instead, eliminating complexity in which the entire rolled material has poor quality.

Similarly, cooling water on the upper surface of the rolled material 8 flows down from both edges of the rolled material 8 in the width direction; hence, both edges of the rolled material 8 in the width direction are strongly cooled compared with the middle portion in the width direction, thereby forming localized low-temperature portions. Also, these portions may not be subjected to quality determination.

For these cases described above, the length of the leading end region of the rolled material, the length of the trailing end region of the rolled material, the width of each edge or one edge of the rolled material, and the like are preferably stored in, for example, the process computer 70 for each type and dimension of the rolled material 8 and are preferably transmitted to a business computer 90 or a personal computer, as needed. Alternatively, these values are preferably transmitted to a near-infrared camera via the controller 50, as needed.

To eliminate abnormal values and noise, furthermore, an upper-temperature-limit-filtering value higher than the upper temperature threshold, a lower-temperature-limit-filtering value lower than the lower temperature threshold, a filtering value for the longitudinal dimension of the out-of-tolerance portion being higher than the threshold $L_{NG}$ of the longitudinal dimension of the out-of-tolerance portion, a filtering value for the width dimension of the out-of-tolerance portion being higher than the threshold $W_{NG}$ of the width dimension of the out-of-tolerance portion, and the like may be stored in, for example, the process computer 70 and may be transmitted to a business computer 90 or a personal computer, as needed. Alternatively, these values may also be transmitted to a near-infrared camera via the controller 50, as needed.

The outline of how the quality is determined on the basis of the planar (two-dimensional) temperature distribution measured with the near-infrared camera and exemplary processes performed in some steps according to the examples have been described above. However, the examples described above are merely illustrative. For example, the specific logic for determining the quality is not limited to the examples.

EXAMPLES

Example 1

Figure 13:
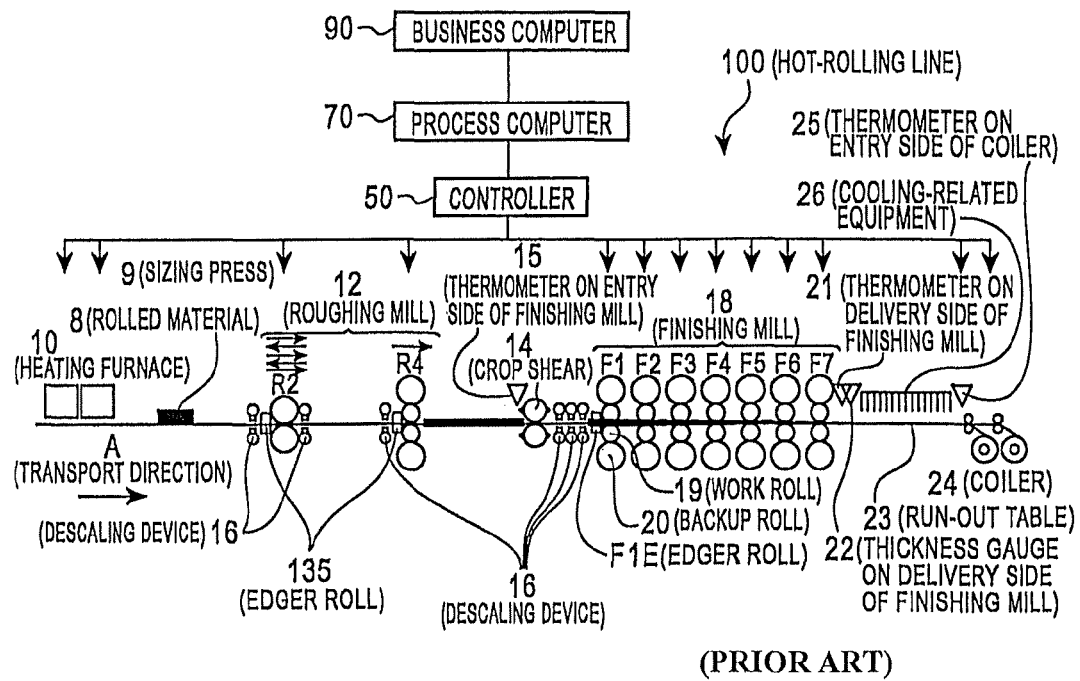
FIG. 13 shows an illustration of an example of a conventional hot-rolling line.
Figure 14:
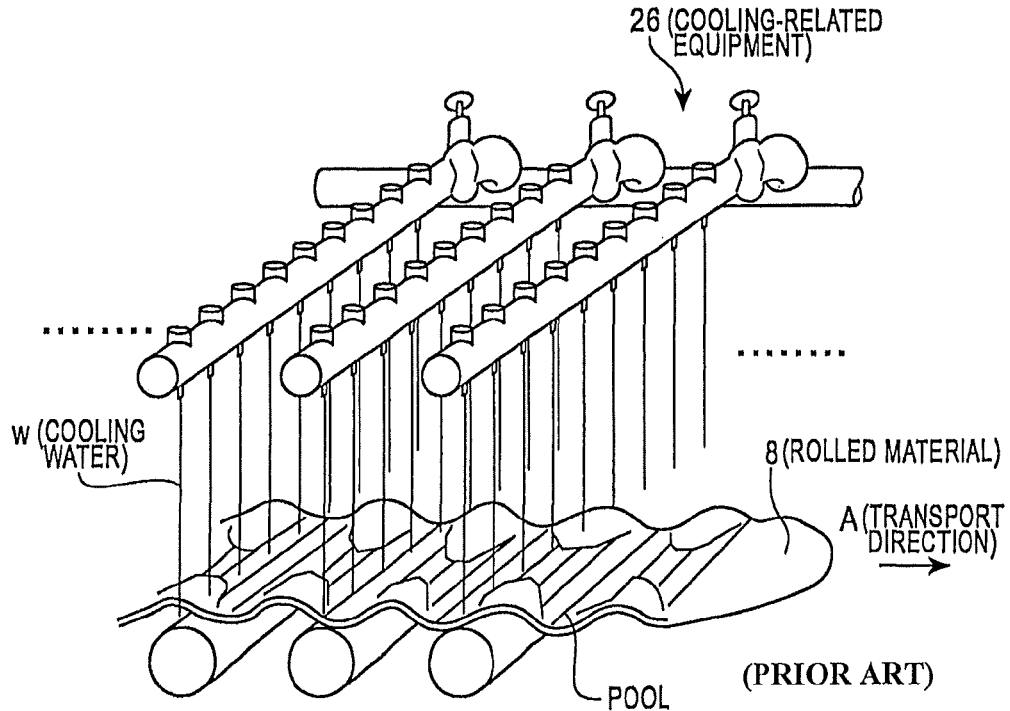
FIG. 14 shows an illustration of problems of the conventional art.
Figure 15A:
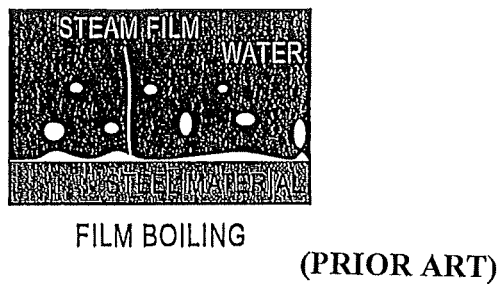
FIGS. 15a and 15b show an illustration of the comparison between film boiling and nucleate boiling.
Figure 15B:
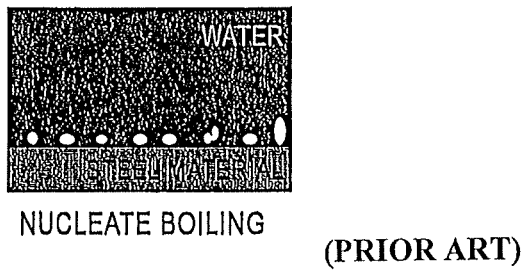
Figure 16:
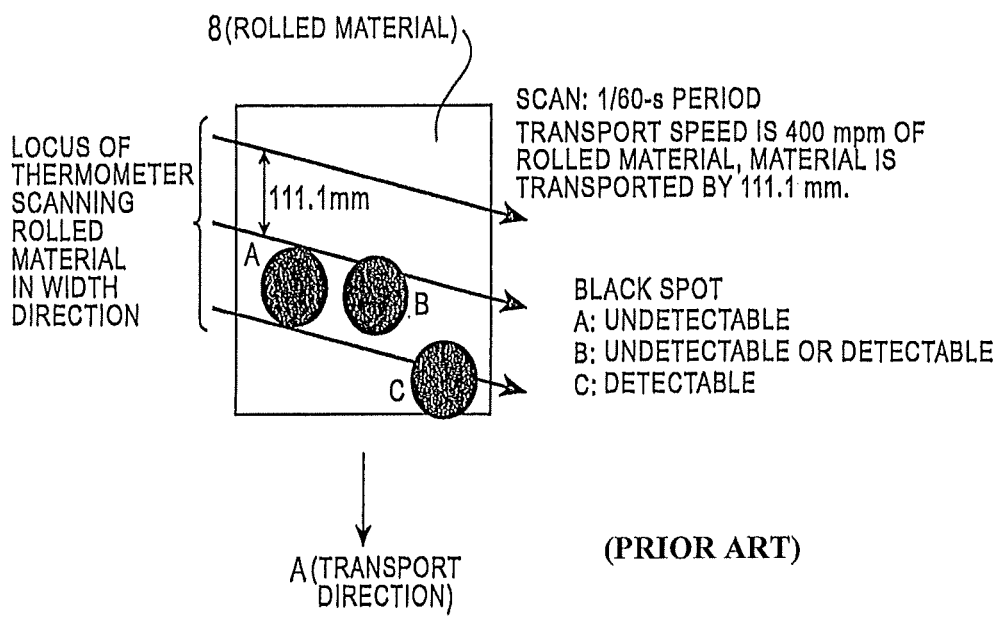
FIG. 16 shows an illustration of problems of the conventional art.
Figure 17A:
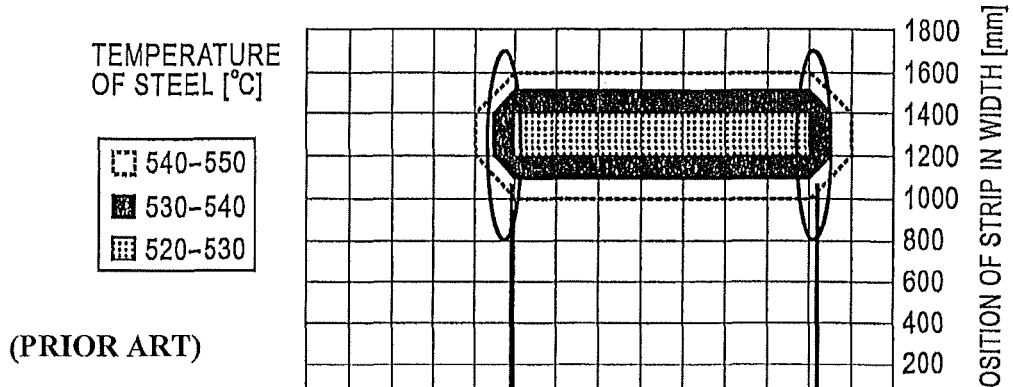
FIGS. 17a and 17b illustrate the conventional art.
Figure 17B:
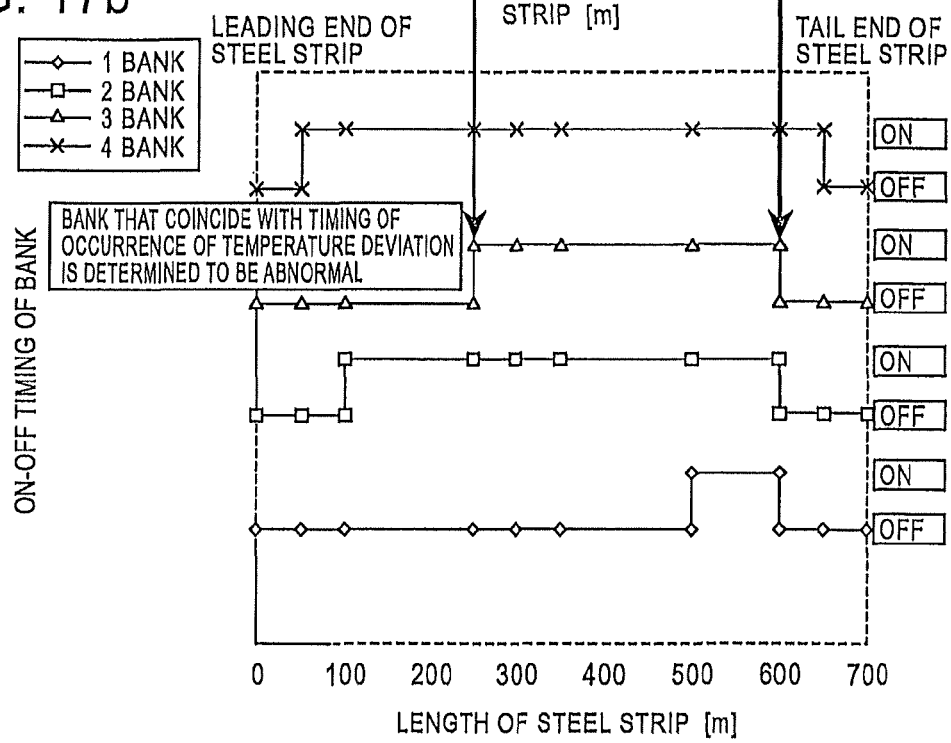

FIG. 9a shows the downstream portion of the finishing mill 18 of the hot-rolling line 100 shown in FIG. 13 described above. As shown in FIG. 9a, the near-infrared camera 25A was located adjacent to the thermometer 25 arranged on the entry side of the coiler. The distance between the near-infrared camera 25A and the thermometer 25 is only 1 m.

Planar (two-dimensional) temperature data of the rolled material 8 measured with the near-infrared camera 25A is sent to a dedicated personal computer 251 and subjected to image processing. With respect to a defective-quality portion of the rolled material 8 being out of a temperature tolerance, its starting point from the leading end of the rolled material 8 and its length are determined. All the foregoing data including the results of the quality determination for every fixed length (4 m) or every 1 m and the planar (two-dimensional) temperature data of the rolled material 8 are defined as the results of the quality determination of the hot-rolled metal strip and associated with each rolled material 8. Identification data, a coil No., is also associated with each rolled material 8 as a key. When the coil No. is entered, the image-processed planar (two-dimensional) temperature data can be remotely copied from personal computers 253 located in other places, such as offices, e.g., offices of manufacturing sectors and offices of the quality control department, via a private LAN 252. The image-processed temperature data can be replayed on screens of the personal computers 253 of each office. Furthermore, the image-processed temperature data can also be analyzed or processed. Of course, the data can also provide quality assurance for delivering a product to a customer. If a defective-quality portion is present, refining steps such as pickling and a skin pass are added, and an operator can take measures to cut out the defective-quality portion.

The volume of data per rolled material 8 varies depending on the length and is about 20 to 40 MB. Thus, data of about several hundred pieces of the rolled materials can be stored even in a hard disk drive with a small storage capacity of a personal computer. When the target is limited to high-tensile steel, data can be practically stored for several months. As described above, even when a storage capacity to the extent of a personal computer is used, an electronic computer system 900 configured to record the determination result of the quality of the hot-rolled metal strip can be established while using the near-infrared camera capable of photographing the entire width of the hot-rolled metal strip in the hot-rolling line.

Example 2

FIG. 9b shows an exemplary arrangement in which the near-infrared camera 21A and the near-infrared camera 25A are located adjacent to the thermometer 21 arranged on the delivery side of the finishing mill and the thermometer 25 arranged on the entry side of the coiler, respectively.

Planar (two-dimensional) temperature data of the rolled material 8 measured with the near-infrared cameras 21A and 25A is transmitted to the dedicated personal computer 251. The subsequent process is the same as in EXAMPLE 1.

The image-processed temperature data can be analyzed or processed and can also provide quality assurance for delivering a product to a customer. The implementation of feedforward control in which the degree of cooling of a portion of the rolled material 8 including a black spot with the cooling-related equipment 26 is reduced on the basis of temperature data measured with the near-infrared camera 21A located adjacent to the thermometer 21 arranged on the delivery side of the finishing mill allows the temperature of the rolled material 8 immediately before coiling to be uniformized to the extent possible and allows the entire length and width of the rolled material 8 to achieve an acceptable quality level to the extent possible.

Example 3

FIG. 9c shows an exemplary arrangement in which the near-infrared camera 27A and the near-infrared camera 25A are located adjacent to the thermometer 27 located at an intermediate point and the thermometer 25 arranged on the entry side of the coiler, respectively. Planar (two-dimensional) temperature data of the rolled material 8 measured with the near-infrared cameras 27A and 25A is transmitted to the dedicated personal computer 251. The subsequent process is the same as in EXAMPLES 1 and 2.

The image-processed temperature data can be analyzed or processed and can also provide quality assurance for delivering a product to a customer. It is possible to perform feedforward control in which a portion of the rolled material 8 located in the upstream region or downstream region of the cooling-related equipment 26 relative to the thermometer 27 located at the intermediate point is cooled on the basis of the temperature data measured with the thermometer 21 arranged on the delivery side of the finishing mill. For example, it is possible to perform feedforward control in which the degree of cooling of a portion of the rolled material 8 including a black spot with the downstream portion of the cooling-related equipment 26 relative to the thermometer 27 located at the intermediate point is reduced on the basis of the temperature data measured with the near-infrared camera 27A located adjacent to the thermometer 27 located at the intermediate point. It is also possible to perform feedback control in which the degree of cooling of a portion of the rolled material 8 including a black spot with the upstream portion of the cooling-related equipment 26 relative to the thermometer 27 located at the intermediate point is reduced. In this way, more assuredly, the temperature of the rolled material 8 immediately before coiling can be uniformized to the extent possible, and the entire length and width of the rolled material 8 can achieve an acceptable quality level to the extent possible.

Example 4

FIG. 9d shows an exemplary arrangement in which the near-infrared cameras 21A, 27A, and 25A are located adjacent to the thermometer 21 arranged on the delivery side of the finishing mill, the thermometer 27 located at the intermediate point, and the thermometer 25 arranged on the entry side of the coiler, respectively.

In EXAMPLE 3 shown in FIG. 9c, more assuredly, the implementation of the same control as in EXAMPLE 3 on the basis of temperature data measured with the near-infrared camera 21A in place of the thermometer 21 arranged on the delivery side of the finishing mill allows the temperature of the rolled material 8 immediately before coiling to be uniformized to the extent possible and allows the entire length and width of the rolled material 8 to achieve an acceptable quality level to the extent possible.

Example 5

Figure 10:
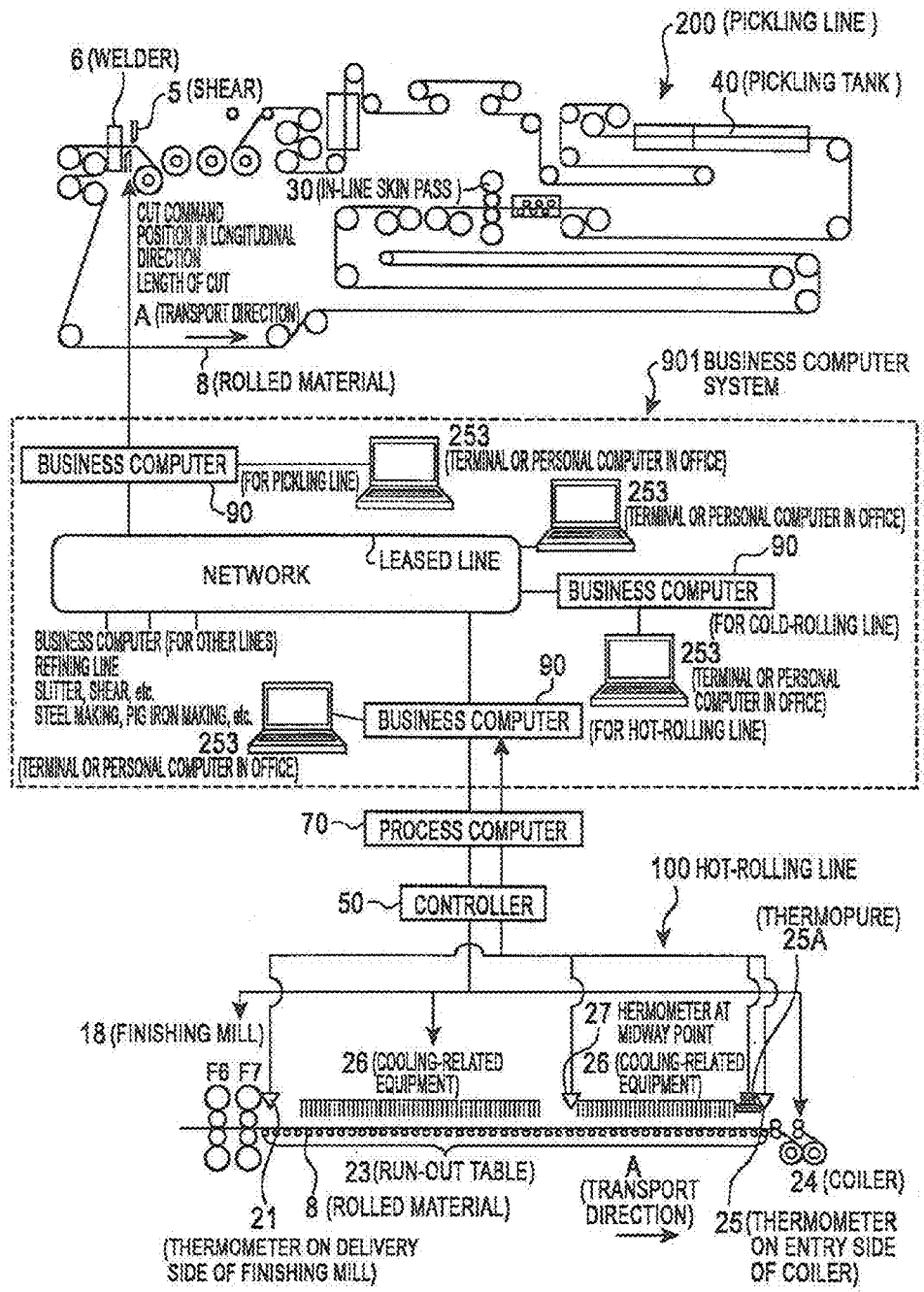
FIG. 10 shows an illustration of another of our structures.

As shown in FIG. 10, temperature data measured with a near-infrared camera is retrieved via the controller 50. The role of the dedicated personal computer 251 in EXAMPLES 1 to 4 shown in FIGS. 9a, 9b, 9c, and 9d is played by the process computer 70 or the business computers 90. Temperature data is recorded in the business computers 90 using identification data, a coil No., associated with each rolled material 8 as a key.

Alternatively, the following process may be performed: The dedicated personal computer 251 (not shown) is interposed between the near-infrared camera and the controller 50, between the controller 50 and the process computer 70, or between the process computer 70 and a corresponding one of the business computers 90. Image-processed temperature data with the dedicated personal computer 251 is transmitted to the business computers 90. The image-processed temperature data is further recorded in the business computers 90 using identification data, a coil No., associated with each rolled material 8 as a key.

A network connected to the business computers 90 for lines via a leased line is formed in place of the private LAN 252 shown in FIG. 9a. The coil No. is entered from a terminal or a personal computer connected to each of the business computer 90 for the lines or a terminal or a personal computer directly connected to the network. For example, the image-processed planar (two-dimensional) temperature data can be remotely copied even when an operator is in a far place, such as an office, e.g., an office of a manufacturing sector and an office of the quality control department. The image-processed temperature data can be replayed on screens of the terminals and the personal computers in the offices. Furthermore, the image-processed temperature data can also be analyzed or processed. Of course, the data can also provide quality assurance for delivering a product to a customer.

In the case where a defective-quality portion is automatically determined to be present, according to a command from a corresponding one of the business computers 90, it is possible to automatically take measures such that, for example, refining steps such as a pickling line 200 including an in-line skin pass 30 are added to cut out the defective-quality portion with a shear 5.

In the case where many defective-quality portions are present in a region located within 30 m from the leading end of the rolled material 8, the 30-m region is cut out. Then the leading end of the rolled material 8 after cutting out the defective-quality portions is joined to a trailing end of a preceding rolled material by welding with a welder 6. The resulting rolled material is allowed to pass continuously through the pickling line 200.

However, for example, in the case where defective-quality portions are present in a region located between 30- and 40-m positions and a region located between 100- and 120-m positions from the leading end of the rolled material 8, when the region located between 30- and 40-m positions and the region located between 100- to 120-m positions are cut out, the resulting 60-m acceptable portion is located between 40- and 100-m positions. In the case of an order from a customer in which a weld may be present, an order from a customer in which a weld must not be present but in which the lightweight 60-m portion is acceptable, or an order in which a strip material is finally produced, the 60-m acceptable portion is joined to leading and trailing ends of the preceding and succeeding rolled materials by welding with the welder 6. The resulting rolled material is allowed to pass continuously through the pickling line 200.

In the case of an order from a customer in which a weld must not be present or the lightweight 60-m portion is not acceptable, a region located between 30- and 100-positions is cut out. The leading end of the rolled material 8 after cutting out the defective-quality portions is joined to a trailing end of a preceding rolled material by welding with the welder 6. The resulting rolled material is allowed to pass continuously through the pickling line 200.

The same is true for the trailing end of the rolled material 8.

In the case of providing instructions for automatically cutting out a defective-quality portion with the shear 5, a cut command, a command for indicating a portion to be cut out from the rolled material in the longitudinal direction, a command for indicating a position in the longitudinal direction (starting point of cut), and a command for indicating the cut-out length are provided.

Various enormous amount of manufacture history data such as attribute data, e.g., the ordered quality, ordered thickness, and ordered width of the rolled material 8 from a customer, and such as a thickness distribution over the entire length and a temperature distribution of the entire width measured with a near-infrared camera in the hot-rolling line 100, are recorded in the business computers 90, the data being associated with each rolled material 8. The business computers 90 are configured to control manufacture and quality histories and to control passing-step instructions in all production steps including the hot-rolling line 100, the pickling line 200, and other production steps such as cold rolling (not shown here).

An electronic computer system including the business computer 90 that serves a series of functions, a computer program therefor, a recording device and a recording medium, a terminal and a personal computer connected thereto, and a man-machine data interface function such as a screen-display function is referred to as an electronic computer system.

FIG. 10 shows the outline of an electronic computer system 901 configured to control manufacture and quality histories and to control passing-step instructions for the hot-rolling line 100 and other production steps.

In an example shown in FIG. 10, the business computers 90 are arranged to control a hot-rolling line, a cold-rolling line, a pickling line, and other lines. The assignment of the roles is not limited to the above example. Alternatively, a single computer may fulfill all roles.

Furthermore, an exemplary structure in which a near-infrared camera is arranged on the hot-rolling line 100 shown in FIG. 10 follows the structure shown in FIG. 9*a*. However, the exemplary structure may follow the structures shown in FIGS. 9*b*, 9*c*, and 9*d*.

Advantages of the implementation of our structures will be described below.

Figure 11:
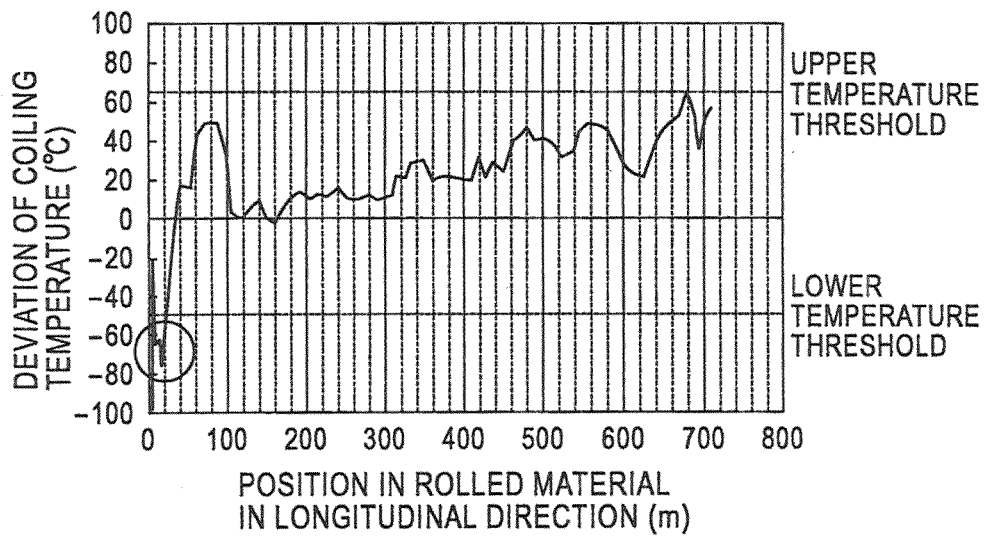
FIG. 11 shows the temperature distribution of the laterally central portion of the rolled material 8 on the entry side of a coiler in the longitudinal direction.

FIG. 11 shows the temperature distribution of the laterally central portion of the rolled material 8 on the entry side of the coiler in the longitudinal direction. This rolled material includes center buckles. There is a correlation between the flatness (steepness) distribution of the laterally central portion of the rolled material in the longitudinal direction and the temperature distribution of the rolled material in the longitudinal direction. It is found that a localized low-temperature portion of the rolled material is formed in a poor-flatness portion located within 20 m from the leading end of the rolled material. In fact, a portion indicated by an open circle was cut out. Pressing the portion under the same conditions as those in a customer caused cracks.

Figure 12:
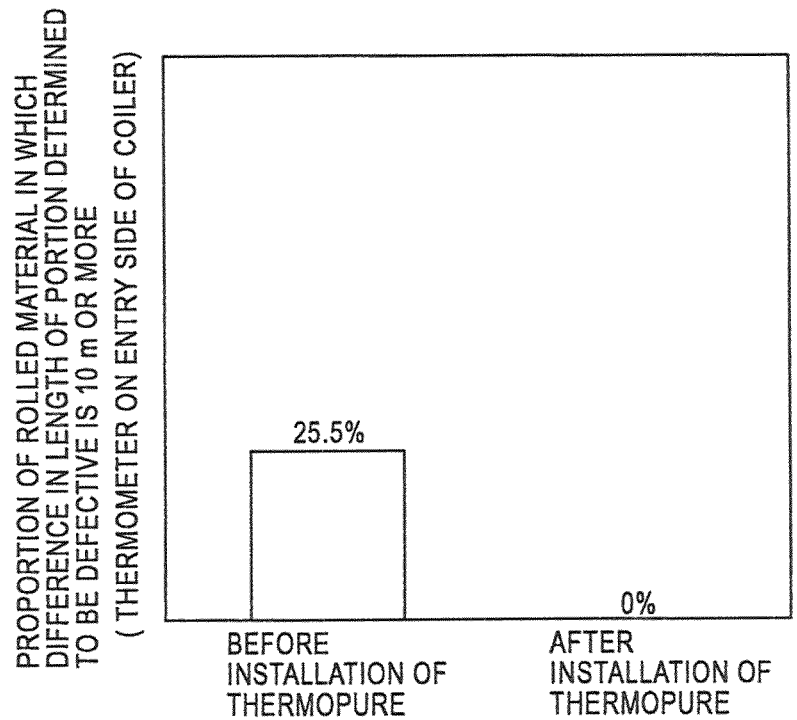
FIG. 12 shows an error comparison between lengths of portions determined to be defective by only a thermometer 25 arranged on the entry side of a coiler and lengths of portions determined to be defective by the thermometer together with a near-infrared camera.

Before installation of the near-infrared camera on the entry side of the coiler, defective-quality portions were determined only by the results of temperature measurement with the thermometer 25 arranged on the entry side of the coiler. FIG. 12 shows the error comparison between lengths of portions determined to be defective by only the thermometer 25 arranged on the entry side of the coiler and lengths of portions determined to be defective by the thermometer together with the near-infrared camera. The vertical axis of FIG. 12 represents the proportion of the number of rolled materials in which the difference when a length of a portion determined to be defective by the temperature measurement with the thermometer 25 arranged on the entry side of the coiler is subtracted from a length of a portion determined to be defective by the temperature measurement with the near-infrared camera is 10 m or more. That is, before installation of the near-infrared camera on the entry side of the coiler, with respect to 25.5% of rolled materials, a portion with a temperature exceeding the upper temperature threshold and a portion with a temperature lower than the lower temperature threshold were improperly determined. (After installation of the near-infrared camera on the entry side of the coiler, naturally, the proportion is 0%.)

INDUSTRIAL APPLICABILITY

The entire width of a hot-rolled metal strip is photographed with a near-infrared camera arranged on the entry side of a coiler of a hot-rolling line and the temperature distribution is measured and/or recorded, which provide proper quality assurance for delivering a product to a customer. In particular, a localized low-temperature portion, a black spot, can be assuredly detected.

The invention claimed is:
1. A method for detecting a low-temperature portion of a hot-rolled metal strip, the method comprising:
    arranging a near-infrared camera at at least one position selected from an entry side of a coiler of a hot-rolling line, a midway point of a run-out table, and a delivery side of a finishing mill;
    arranging a spot thermometer at the at least one position;
    measuring a luminance of a portion of a heat source with the near-infrared camera;
    measuring a temperature of the portion of the heat source with the spot thermometer;
    storing in a computer a luminance-temperature conversion curve showing a relationship between the luminance measured with the near-infrared camera and the temperature measured with the spot thermometer for the portion of the heat source;
    obtaining an image of an entire width of a hot-rolled metal strip with the near-infrared camera at the at least one position;
    converting a luminance in the image obtained with the near-infrared camera into a temperature using the luminance-temperature conversion curve; and
    detecting a low-temperature portion of the hot-rolled metal strip based on the converted temperature for down- stream removal of a defective quality portion corresponding to the detected low-temperature portion of the hot-rolled metal strip.

2. The method according to claim 1, further comprising measuring a temperature of a rolled material by photographing the rolled material with the near-infrared camera arranged at at least one position selected from the entry side of the coiler of the hot-rolling line, the midway point of the run-out table, and the delivery side of the finishing mill, the near-infrared camera being capable of photographing the entire width of the hot-rolled metal strip; measuring a temperature of a portion of the rolled material with the spot thermometer arranged at the position where the near-infrared camera is arranged, the portion being in the field of view of the near-infrared camera; calibrating the near-infrared camera in such a manner that the temperature of the portion of the rolled material measured with the near-infrared camera coincides with the temperature of the same portion measured with the spot thermometer; and photographing the rolled material.

3. The method according to claim 1, further comprising recording a photographic result of a low-temperature portion of a hot-rolled metal strip.

4. The method according to claim 1, further comprising adjusting the shutter speed of the near-infrared camera in response to temperature of the hot-rolled metal strip so that the temperature of the hot-rolled metal strip is within a measurable temperature range when the entire width of the hot-rolled metal strip is photographed with the near-infrared camera arranged on the entry side of the coiler of the hot-rolling line.

5. The method according to claim 1, further comprising selecting the shutter speed of the near-infrared camera such that a predetermined resolution of the temperature measured by photographing the entire width of the hot-rolled metal strip with the near-infrared camera is achieved.

6. The method according to claim 1, further comprising photographing an entire length of the hot-rolled metal strip.

7. The method according to claim 1, further comprising removing from the hot-rolled metal strip the defective quality portion corresponding to the detected low-temperature portion of the hot-rolled metal strip.

8. The method according to claim 7, wherein the removing step includes cutting out the defective quality portion from the hot-rolled metal strip in a downstream step.

9. The method according to claim 1, further comprising adjusting a shutter speed of the near-infrared camera in response to the temperature measured with the spot thermometer.

10. A method for detecting a low-temperature portion of a hot-rolled metal strip, the method comprising:
- arranging a near-infrared camera at at least one position selected from an entry side of a coiler of a hot-rolling line, a midway point of a run-out table, and a delivery side of a finishing mill;
- arranging a spot thermometer at the at least one position;
- measuring a temperature of a portion of a rolled material by photographing the rolled material with the near-infrared camera;
- measuring a temperature of the portion of the rolled material with the spot thermometer;
- calibrating the near-infrared camera in such a manner that the temperature of the portion of the rolled material measured with the near-infrared camera coincides with the temperature of the portion of the rolled material measured with the spot thermometer;
- obtaining an image of an entire width of a hot-rolled metal strip with the near-infrared camera at the at least one position; and
- detecting a low-temperature portion of the hot-rolled metal strip for downstream removal of a defective quality portion corresponding to the detected low-temperature portion of the hot-rolled metal strip.

* * * * *